US009575087B2

(12) United States Patent
Schick et al.

(10) Patent No.: US 9,575,087 B2
(45) Date of Patent: Feb. 21, 2017

(54) RISK-MANAGED, SINGLE-USE, PRE-CALIBRATED, PRE-STERILIZED SENSORS FOR USE IN BIO-PROCESSING APPLICATIONS

(71) Applicant: Parker-Hannifin Corporation, Cleveland, OH (US)

(72) Inventors: Karl G. Schick, Madison, WI (US); David Uhen, Burlington, WI (US)

(73) Assignee: Parker-Hannifin Corporation, Cleveland, OH (US)

( * ) Notice: Subject to any disclaimer, the term of this patent is extended or adjusted under 35 U.S.C. 154(b) by 566 days.

(21) Appl. No.: 13/964,833

(22) Filed: Aug. 12, 2013

(65) Prior Publication Data

US 2014/0060161 A1 Mar. 6, 2014

Related U.S. Application Data

(60) Provisional application No. 61/697,421, filed on Sep. 6, 2012, provisional application No. 61/788,708, filed on Mar. 15, 2013.

(51) Int. Cl.
*G01N 27/10* (2006.01)
*G01N 37/00* (2006.01)
(Continued)

(52) U.S. Cl.
CPC ............... *G01N 37/00* (2013.01); *G01F 1/00* (2013.01); *G01N 27/10* (2013.01);
(Continued)

(58) Field of Classification Search
CPC .... F01N 11/007; F01N 2560/20; G01N 25/18; G01N 27/4067; G01N 21/532; G01N 21/534; G01N 21/53; G01N 21/49; G01N 21/8507; G01N 27/10; G01N 2021/4707; G01N 2021/4709; G01N 2021/4711; G01N 2021/4726; G01N 2021/4769; G01N 2021/5969; G01N 2201/0639; G05D 23/24; Y02T 10/47
See application file for complete search history.

(56) References Cited

U.S. PATENT DOCUMENTS 2,892,378 A 6/1959 Canada
4,040,743 A 8/1977 Villaume et al.
(Continued)

FOREIGN PATENT DOCUMENTS

DE 4 242 927 6/1994
EP 0 344 430 A2 6/1989
(Continued)

OTHER PUBLICATIONS

Korean Patent Abstract Publ. No. 1020030066373, Sep. 8, 2003, Elektromanufaktur.
(Continued)

*Primary Examiner* — Hezron E Williams
*Assistant Examiner* — Gedeon M Kidanu
(74) *Attorney, Agent, or Firm* — Cook Alex Ltd.

(57) ABSTRACT

Single-use, pre-sterilized, and pre-calibrated, pre-validated sensors are provided. These sensors are designed to store sensor-specific information, such as calibration and production information, in a non-volatile memory chip on the sensor or in a barcode printed on the sensor. These sensors may be utilized with in-line systems, closed fluid circuits, bioprocessing systems, or systems which require an aseptic environment while avoiding or reducing cleaning procedures and quality assurance variances. The sensors exhibit both their primary sensing function such as conductivity, pH level, dissolved oxygen, pressure or temperature, as well as at least one secondary sensing function of risk management or risk mitigation.

24 Claims, 11 Drawing Sheets

(51) Int. Cl.
  *G06F 19/00*    (2011.01)
  *G01N 27/416*   (2006.01)
  *G01F 1/00*     (2006.01)

(52) U.S. Cl.
  CPC ....... *G01N 27/4163* (2013.01); *G06F 19/366* (2013.01); *A61B 2560/028* (2013.01)

(56) References Cited

U.S. PATENT DOCUMENTS

| | | | |
|---|---|---|---|
| 4,725,148 A | 2/1988 | Endo et al. | |
| 5,140,168 A | 8/1992 | King | |
| 5,446,531 A | 8/1995 | Boyer et al. | |
| 5,485,013 A | 1/1996 | Cummins | |
| 5,596,408 A | 1/1997 | Cummins et al. | |
| 5,757,481 A | 5/1998 | O'Brien et al. | |
| 5,828,458 A | 10/1998 | Taylor et al. | |
| 5,923,433 A | 7/1999 | Giuffre et al. | |
| 5,947,689 A | 9/1999 | Schick | |
| 5,991,355 A * | 11/1999 | Dahlke | A61B 18/14 377/15 |
| 6,166,538 A | 12/2000 | D'Alfonso | |
| 6,298,255 B1 | 10/2001 | Cordero et al. | |
| 6,308,089 B1 * | 10/2001 | von der Ruhr | A61B 5/00 600/338 |
| 6,350,382 B1 | 2/2002 | Schick | |
| 6,375,847 B1 | 4/2002 | Hartmann | |
| 6,456,375 B1 | 9/2002 | Ottens et al. | |
| 6,509,558 B1 | 1/2003 | Loch et al. | |
| 6,553,241 B2 | 4/2003 | Mannheimer et al. | |
| 6,567,166 B2 | 5/2003 | Ottens et al. | |
| 6,712,963 B2 * | 3/2004 | Schick | A61M 1/0209 210/137 |
| 6,833,555 B2 | 12/2004 | Schenkl | |
| 6,842,243 B2 | 1/2005 | Tokhtuev et al. | |
| 6,891,619 B2 | 5/2005 | Durfee et al. | |
| 7,001,513 B2 * | 2/2006 | Bell | A61M 1/02 210/143 |
| 7,052,603 B2 | 5/2006 | Schick | |
| 7,142,299 B2 | 11/2006 | Tukhtuev et al. | |
| 7,287,699 B2 * | 10/2007 | Liu | G01F 25/0007 235/375 |
| 7,400,986 B2 | 7/2008 | Latham et al. | |
| 7,410,587 B2 | 8/2008 | Schick | |
| 7,788,047 B2 * | 8/2010 | Schick | A61M 1/3621 235/375 |
| 7,857,506 B2 | 12/2010 | Schick et al. | |
| 7,880,626 B2 * | 2/2011 | Al-Ali | A61B 5/14551 340/635 |
| 7,927,010 B2 | 4/2011 | Schick et al. | |
| 8,111,131 B2 | 2/2012 | Zaveruha et al. | |
| 8,121,856 B2 | 2/2012 | Huster et al. | |
| 8,501,119 B2 | 8/2013 | Burke et al. | |
| 8,506,162 B2 * | 8/2013 | Schick | A61M 1/3621 324/691 |
| 8,817,259 B2 * | 8/2014 | Schick | G01N 21/0303 356/442 |
| 2003/0117623 A1 | 6/2003 | Tokhtuev et al. | |
| 2005/0190370 A1 | 9/2005 | Ciobanu et al. | |
| 2006/0055927 A1 | 3/2006 | Feng | |
| 2006/0118472 A1 * | 6/2006 | Schick | B01D 61/18 210/198.2 |
| 2007/0126794 A1 * | 6/2007 | Schick | A61M 1/3621 347/44 |
| 2007/0179739 A1 * | 8/2007 | Donofrio | A61B 5/1118 702/160 |
| 2007/0237678 A1 | 10/2007 | Roesicke et al. | |
| 2007/0255527 A1 * | 11/2007 | Schick | A61M 1/3621 702/179 |
| 2008/0021325 A1 * | 1/2008 | Drost | A61B 5/021 600/454 |
| 2008/0088467 A1 * | 4/2008 | Al-Ali | A61B 5/14551 340/679 |
| 2008/0241866 A1 | 10/2008 | Korlach et al. | |
| 2009/0015403 A1 * | 1/2009 | Kuris | G06F 19/3412 340/540 |
| 2011/0004186 A1 * | 1/2011 | Butterfield | G06F 19/366 604/500 |
| 2011/0006878 A1 | 1/2011 | Nyffeler et al. | |
| 2011/0298613 A1 * | 12/2011 | Ben Ayed | A61B 5/002 340/539.11 |
| 2012/0330116 A1 | 12/2012 | Eggers et al. | |

FOREIGN PATENT DOCUMENTS

| | | |
|---|---|---|
| EP | 1 525 138 B1 | 12/2008 |
| EP | 2 012 323 A2 | 1/2009 |
| EP | 2 392 948 A2 | 12/2011 |
| GB | 2 446934 A | 8/2008 |
| JP | 2011 209037 A | 10/2011 |
| JP | 4 991963 B | 8/2012 |
| WO | WO 92/17775 | 10/1992 |
| WO | WO 2013/033212 | 3/2013 |

OTHER PUBLICATIONS

Korean Patent Abstract Publ. No. 1020030068456, Aug. 21, 2003, Electromanufaktur.

Wong et al., Radiation Hard by Design Techniques for EEPROM, 12th NASA Symposium on FLSI Design, Doeur d'Alene, Idaho Oct. 4-5, 2005.

SciCon Conductivity Sensors, Brochure, Scilog, Inc., May 4, 2009.

Written Opinion of the International Preliminary Examining Authority, PCT/US2013/058208, Sep. 16, 2014.

International Search Report and Written Opinion of the International Searching Authority, PCT/US2013/058208, Apr. 15, 2014.

International Preliminary Report on Patentability, PCT/US2013/058208, Dec. 23, 2014.

* cited by examiner

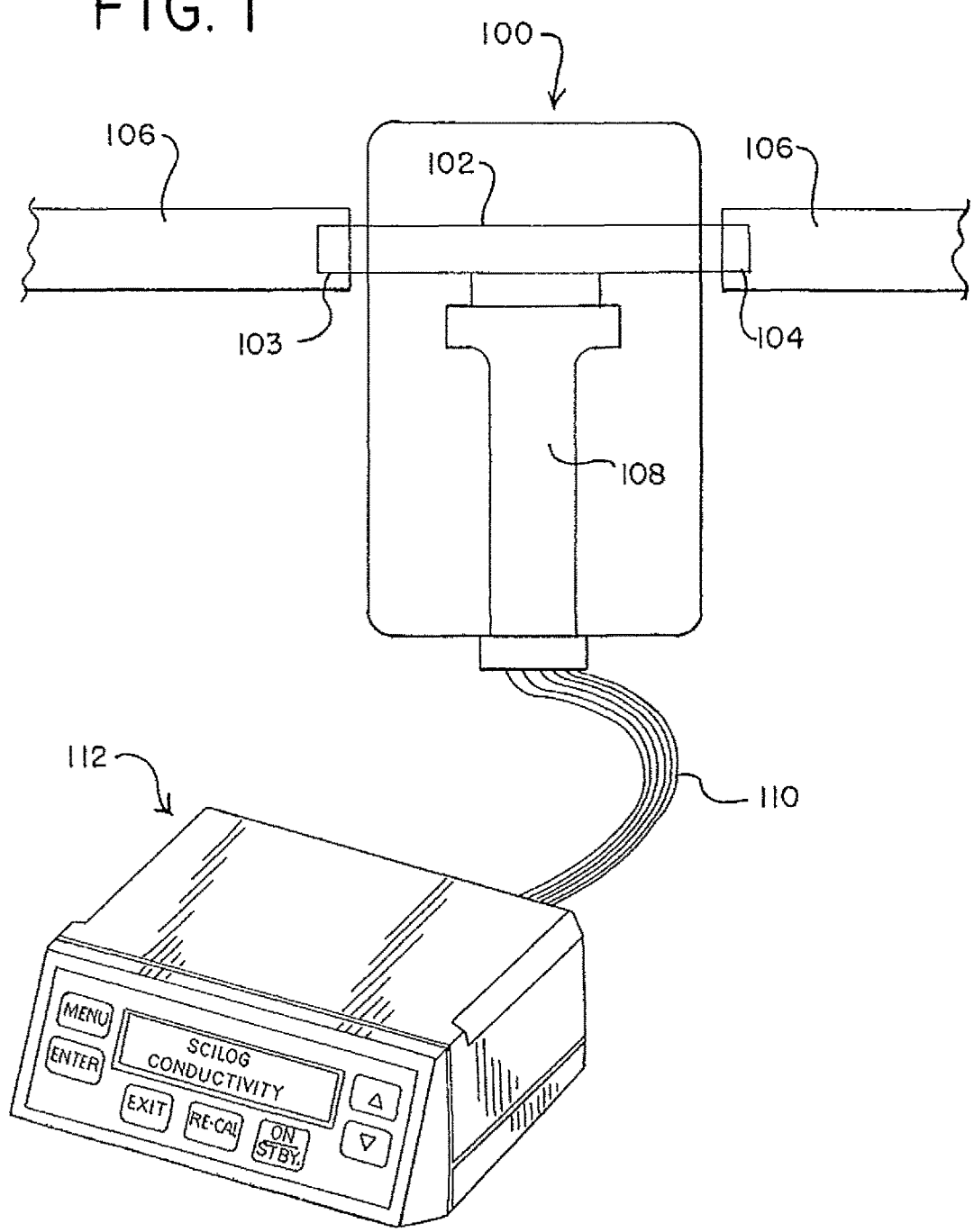

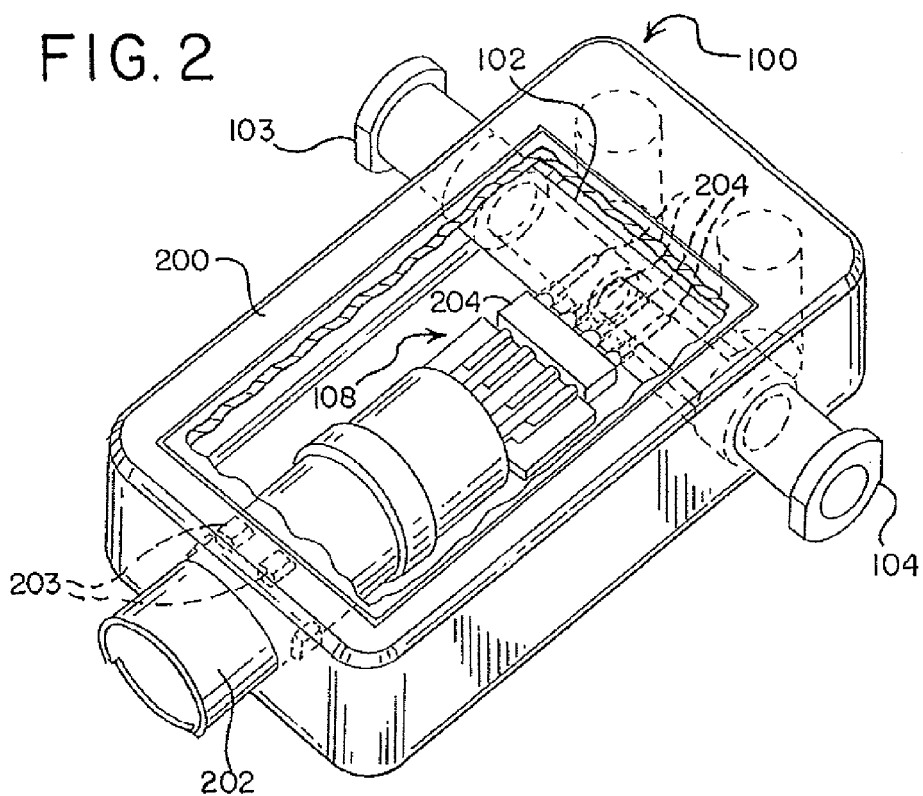
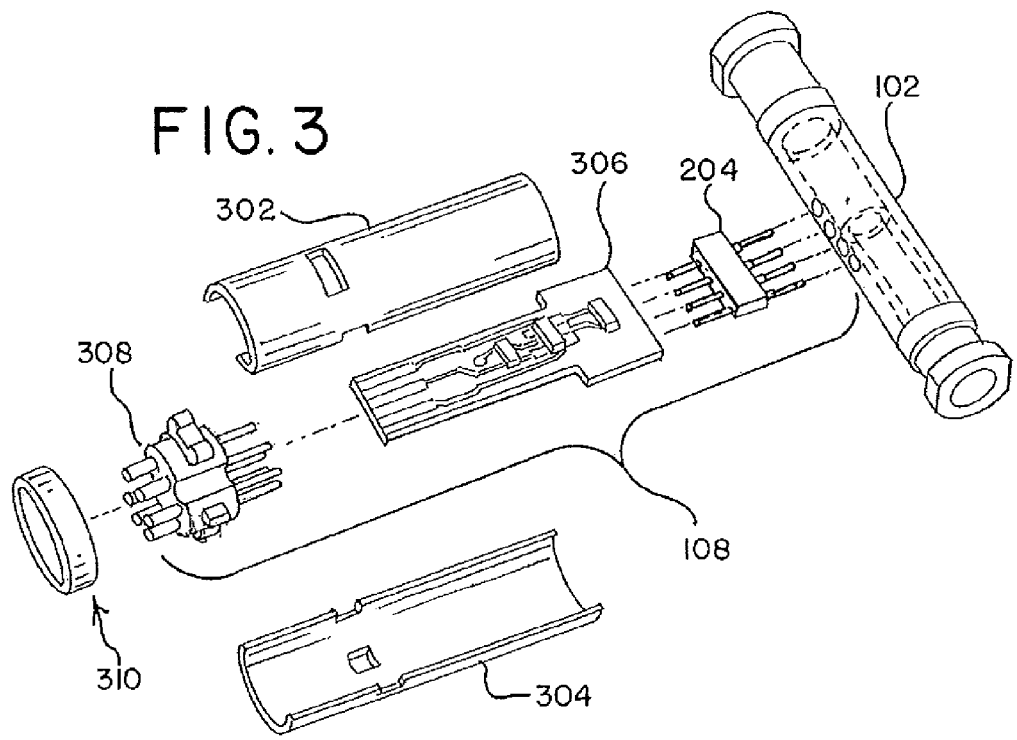

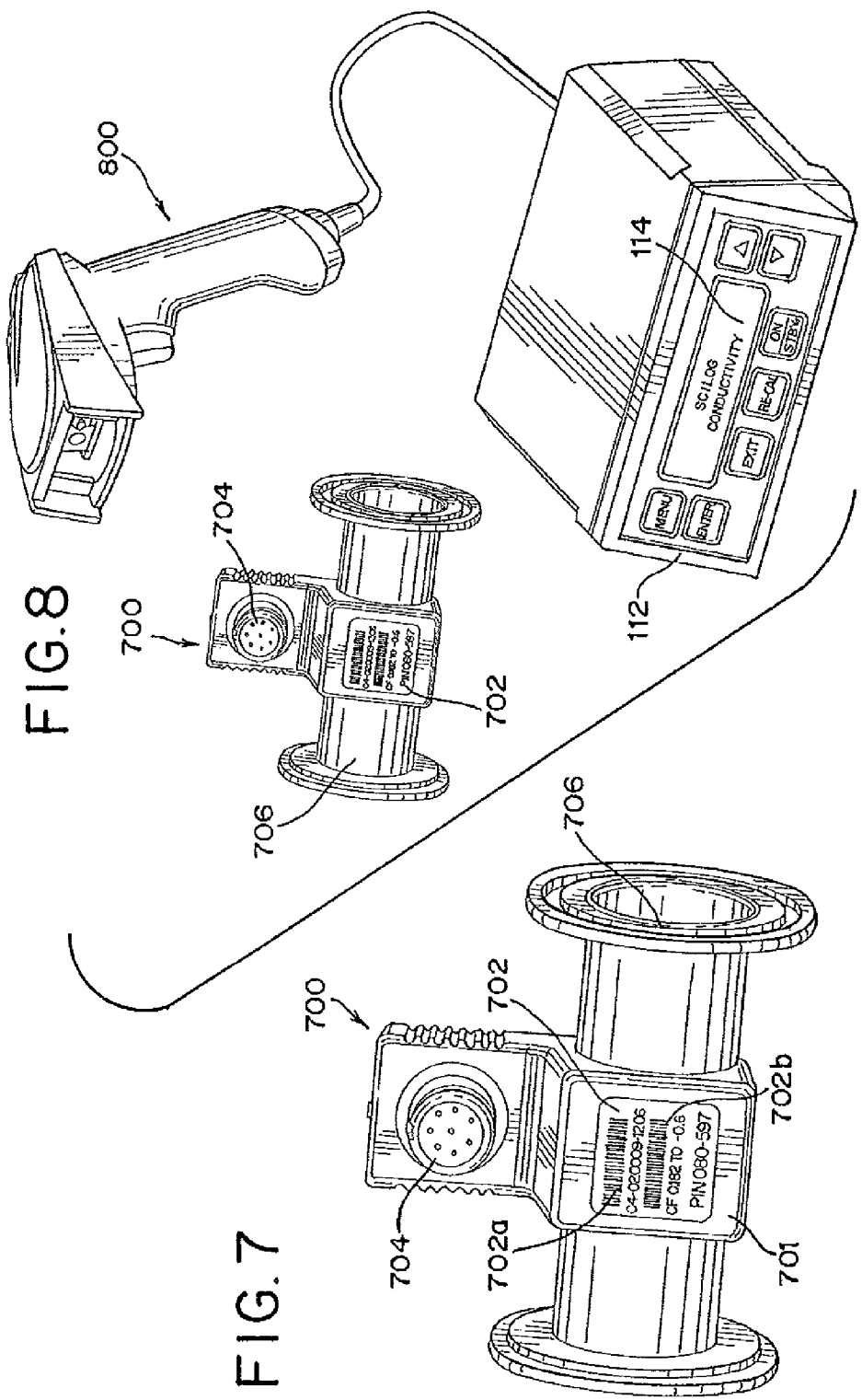

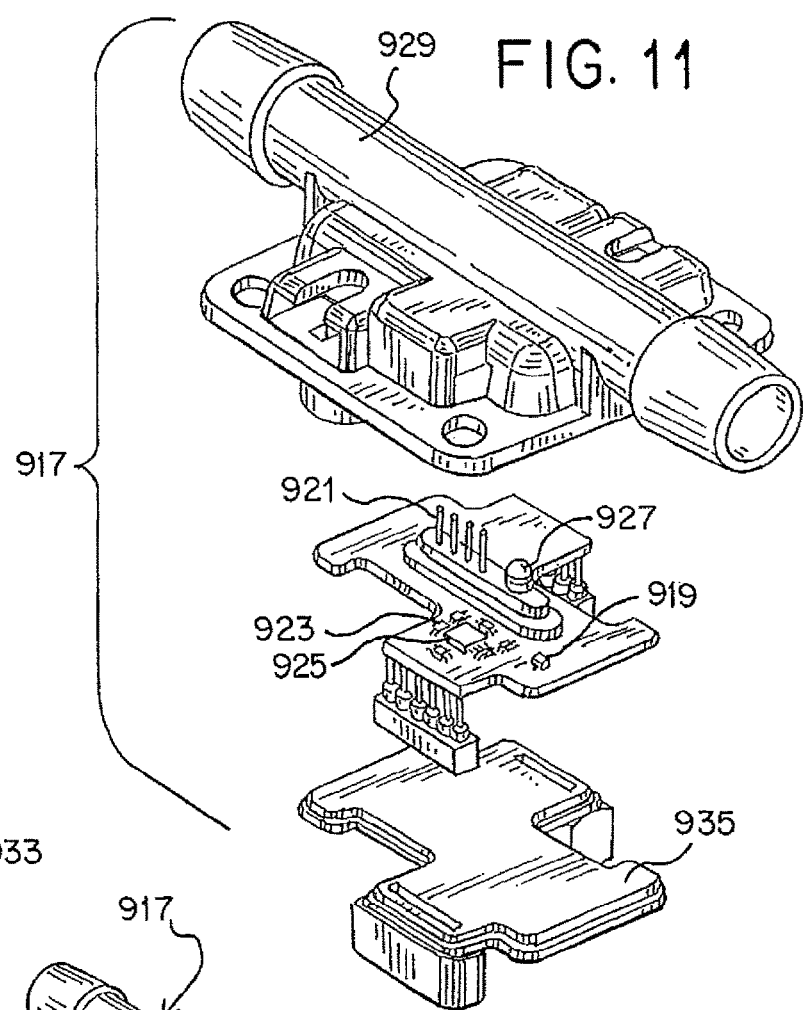
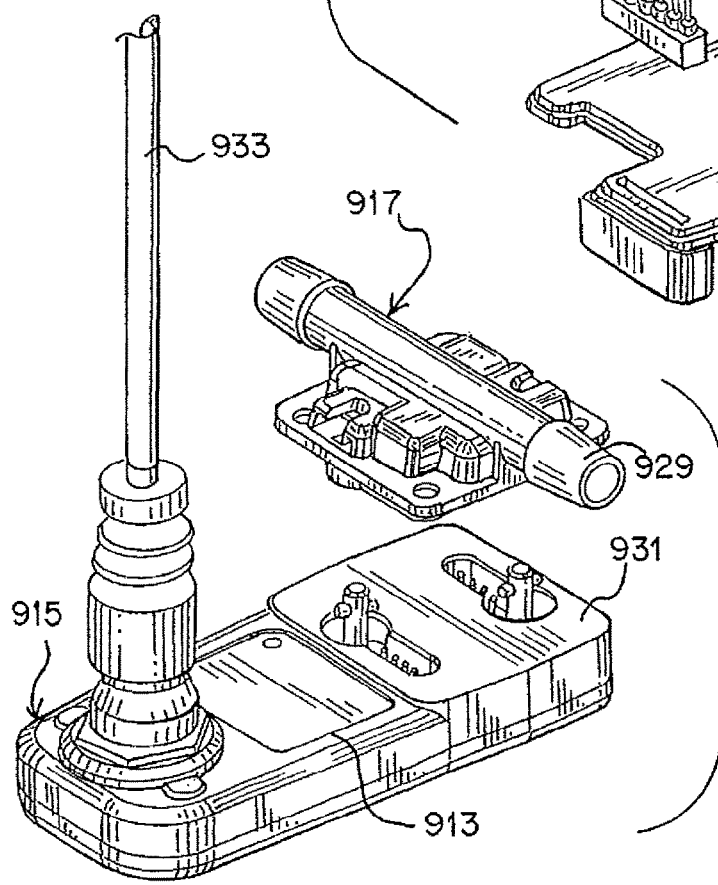

FIG. 12
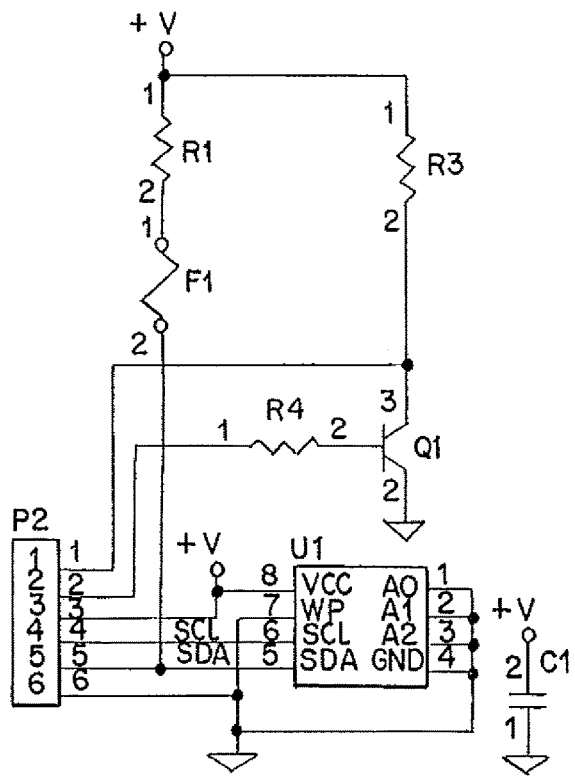
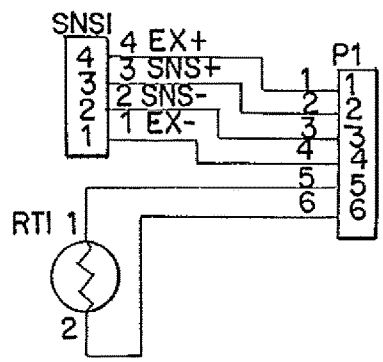
FIG. 13
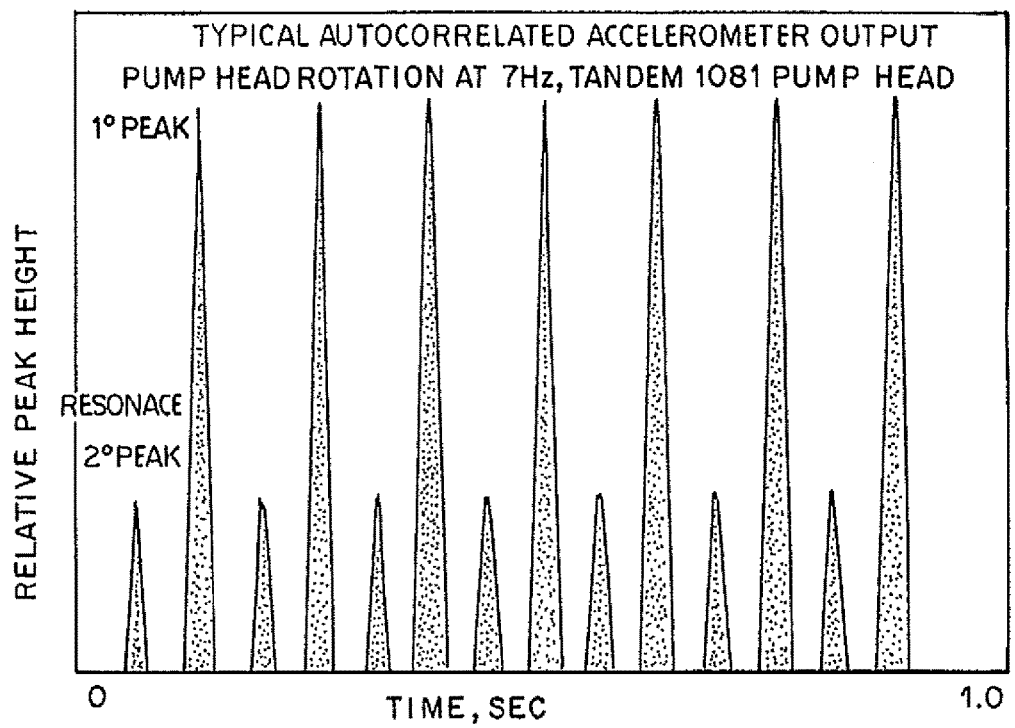

FIG. 16

| SCIPRES LUER SENSORS (22), GAMMA, 35KGY | | | | APPLIED AIR PRESSURE | | | | |
|---|---|---|---|---|---|---|---|---|
| SENSOR ID | CF-1 | CF-2 | PZ | 0.00 PSI | 15.07 PSI | 30.01 PSI | 45.03 PSI | 60.01 PSI |
| S1-290023-1111 | 0.974 | 1.052 | -28 | 0.00 | 15.16 | 30.01 | 44.99 | 60.07 |
| S1-290024-1111 | 0.961 | 1.072 | -21 | 0.00 | 15.20 | 30.08 | 45.07 | 60.26 |
| S1-290025-1111 | 0.983 | 1.037 | -36 | 0.00 | 15.04 | 29.86 | 44.87 | 59.96 |
| S1-290026-1111 | 0.953 | 1.072 | -20 | 0.01 | 15.07 | 29.91 | 44.93 | 60.21 |
| S1-290027-1111 | 1.006 | 1.016 | -29 | 0.00 | 15.04 | 29.86 | 44.84 | 59.89 |
| S1-290028-1111 | 0.951 | 1.037 | -22 | 0.02 | 15.10 | 29.97 | 45.00 | 60.26 |
| S1-290029-1111 | 0.962 | 1.062 | -24 | 0.00 | 15.05 | 29.84 | 44.83 | 60.03 |
| S1-290030-1111 | 0.968 | 1.055 | -30 | 0.01 | 15.07 | 29.91 | 44.95 | 60.16 |
| S1-290031-1111 | 0.965 | 1.056 | -30 | 0.01 | 15.06 | 29.86 | 44.89 | 60.06 |
| S1-290032-1111 | 0.958 | 1.069 | -25 | 0.01 | 15.08 | 29.89 | 44.89 | 60.11 |
| S1-290033-1111 | 1.005 | 1.015 | -22 | 0.00 | 15.06 | 29.88 | 44.86 | 59.90 |
| S1-290034-1111 | 0.965 | 1.070 | -5 | -0.04 | 15.13 | 29.98 | 44.94 | 60.11 |
| S1-290035-1111 | 0.975 | 1.060 | -10 | -0.03 | 15.11 | 29.94 | 44.86 | 59.95 |
| S1-290036-1111 | 0.955 | 1.086 | -3 | -0.05 | 15.21 | 30.11 | 45.06 | 60.21 |
| S1-290037-1111 | 0.970 | 1.060 | -25 | 0.00 | 15.11 | 29.95 | 44.94 | 60.11 |
| S1-290038-1111 | 0.994 | 1.027 | -23 | 0.02 | 15.07 | 29.87 | 44.84 | 59.86 |
| S1-290039-1111 | | SENSOR FAILURE | | | | | | |
| S1-290040-1111 | 1.034 | 0.994 | -34 | 0.00 | 15.15 | 29.99 | 44.90 | 59.79 |
| S1-290041-1111 | 0.951 | 1.087 | -23 | 0.00 | 15.22 | 30.11 | 45.08 | 60.23 |
| S1-290042-1111 | 0.968 | 1.067 | -15 | 0.00 | 15.19 | 30.06 | 45.02 | 60.13 |
| S1-290043-1111 | 0.969 | 1.056 | -25 | 0.00 | 15.09 | 29.92 | 44.95 | 60.12 |
| S1-290044-1111 | 0.967 | 1.061 | -19 | 0.00 | 15.09 | 29.90 | 44.87 | 60.03 |
| GROUP AVERAGE | 0.973 | 1.055 | -22 | 0.00 | 15.11 | 29.95 | 44.93 | 60.07 |
| GROUP STD DEV | 0.021 | 0.024 | 8 | 0.02 | 0.06 | 0.09 | 0.08 | 0.14 |

RISK-MANAGED, SINGLE-USE, PRE-CALIBRATED, PRE-STERILIZED SENSORS FOR USE IN BIO-PROCESSING APPLICATIONS

CROSS REFERENCE TO RELATED APPLICATIONS

This application claims the benefit of U.S. Provisional application Ser. No. 61/697,421, filed Sep. 6, 2012, and Ser. No. 61/788,708, filed Mar. 15, 2013. These applications are incorporated by reference hereinto.

FIELD OF THE DISCLOSURE

The present subject matter generally relates to sensors and methods concerning sensor-specific data collection and to single-use and/or disposable, pre-sterilized in-line sensors. More specifically, the invention relates to single-use and/or disposable, pre-calibrated, pre-sterilized, pre-validated probes or sensors that contain non-volatile memory capable of storing specific conductivity and preferably also information concerning the "out-of-box" performance of the probe or sensor. The subject matter relates to sensors, systems and manifold units with risk management assessment and mitigation functions and involve sensor-specific data collection functions during processing of biopharmaceutical solutions.

BACKGROUND

Pre-sterilized, single-use bag manifolds such as those used in bio-pharmaceutical production (see U.S. Pat. Nos. 6,712,963; 7,052,603 and 7,410,587, incorporated here by reference) lack the ability to monitor and validate important, analytical solution parameters during the processing of biopharmaceutical solutions. Such bag manifolds are used, for example, in preparative chromatography, tangential flow filtration (TFF), normal flow filtration (NFF), centrifugation or fluid transfer.

In-line, flow through-type sensors and detectors are well known in industry and are extensively used in analytical laboratories, pilot plants and production facilities. In-line conductivity detectors, in particular, are used in ion chromatography, preparative chromatography, flow injection analysis (FIA), tangential flow filtration (TFF), as well as water purity analysis. When these are intended for multiple use, typically made out of machined, stainless steel or plastic materials, they are intended for permanent installations and long-term use and are difficult to sterilize, require in-field calibration and validation by an experienced operator before use, and are very expensive, often costing thousands of dollars.

The use of a memory device imbedded in disposable clinical sensors has been reported. For example, U.S. Pat. No. 5,384,028 deals with the fabrication of an enzyme-based glucose biosensor that utilizes a sensor-imbedded data memory device and requires sensor calibration and/or validation by the clinician immediately prior to each use.

In-line sensors for use in bioprocessing applications must be designed to meet government regulations regarding device traceability and validation. In addition, in-line sensors must meet the application requirements for accuracy and precision. These requirements present extra challenges and pose unique problems when the in-line sensor is to be disposable and suitable for single use as desired. Another problem is how to provide disposable in-line sensors that are pre-calibrated. Also for aseptic sensor applications, each single-use sensor, must meet sterilization requirements. Furthermore, single-use sensors must meet economic requirements, i.e. sensors must be low cost, easy to replace with negligible disposal expense.

Meeting sensor sterilization requirements represents another very significant sensor design challenge. This is especially the case, when the sensor is intended for single-use bag manifold applications such as those referenced therein. The biotechnology and bio-pharmaceutical industries utilize four different sterilization methods: (1) autoclaving (i.e. timed exposure to pressurized steam at approximately 125° Celsius); (2) time-limited exposure to an ethylene oxide gas; (3) gamma ray irradiation up to 50 kGy; and (4) electron-beam irradiation.

For many single-use sensor applications, e.g. for bag manifolds, the preferred sterilization method by the industry is by gamma or electron-beam irradiation. The main advantage of gamma and electron-beam irradiation lies is that the entire, pre-assembled manifold, including bags, tubing, connectors and sensors, can be first sealed in a shipping bag or bags and then exposed to sterilizing radiation or electron-beam bombardment. The entire manifold assembly within the shipping bag system remains sterile for a rated period, unless compromised during shipment or storage.

SUMMARY

The present disclosure overcomes the aforementioned shortcomings and problems faced by the industry by providing low-cost, risk-managed, pre-sterilized, pre-calibrated, in-line sensors capable of being traced and validated. The disclosure further provides a data access to on-sensor memory data and device using barcode or other printed means, and/or a sensor-embedded, non-volatile memory chip for storing information for each specific sensor, including device-specific information for instant recall by the user.

One embodiment is an in-line electrical conductivity sensor system used to measure the electrical conductivity of process flow solutions. Other embodiments of the in-line units are for sensing pressure, temperature, pH, dissolved oxygen, solution turbidity and combinations of such properties of the fluid flowing through the sensor.

An embodiment has two main components: the user interface and the sensor assembly module. Such a sensor assembly module contains a short tubular fluid conduit, one or more sensor or probe components, referred to herein at times as a sensor or a sensor component. The sensor assembly module further includes a printed circuit board (PCB) with a sensor-embedded non-volatile memory chip. Sensor components can include electrodes, toroidal sensors or other arrangements. All components are designed or selected for highly automated production methods such as those used in surface mounted electronic assemblies. The present disclosure focuses on multiple electrode arrangements as the preferred embodiment for carrying out the sensing function.

In an illustrated embodiment, four electrodes are press-fitted into and through four, linearly arranged holes in the fluid conduit wall. The electrodes are epoxied, cemented or sealed into place to prevent leaks or contamination. The electrodes are connected to a PCB. The PCB contains a non-volatile memory chip or EEPROM or a FRAM, which is used to store sensor-specific factory calibration data and/or information, which typically include the sensor's ID number, a Cell Constant, a Temperature Offset Value, and the calibration date, as well as risk-management information.

Furthermore, each sensor can exhibit an "out-of-box" performance variance value which is also stored in the non-volatile memory chip. This "out-of-box" value is a statistically derived performance variance (measured for example in 0.100 molar KCl at 25.0° C.) that represents the maximum measurement error for that specific sensor within a 98% confidence limit. The statistically derived variance value is based on the performance analysis of all calibrated sensors within a production run, typically of between about 100 and about 500 sensors. The factory determined performance variance represents a predictive, "out-of-box" sensor performance level.

The user interface performs the conductivity measurement by monitoring the current across the two inner working electrodes. Prior to the conductivity (or other parameter) measurement, the user interface retrieves the Cell Constant from its own memory from the sensor memory or FRAM or has read and/or decoded the barcode and retrieved that information. The measured solution conductance is multiplied by the Cell Constant to arrive at the actual electrical conductivity of the tested process solution. The sensor-specific Cell Constant is determined during factory calibration using a solution (for example 0.100 molar KCl at 25.0° C.) with a known conductivity. The Cell Constant is subsequently stored in the non-volatile memory of the sensor assembly module.

Typically, after the sensor module is prepared, it is placed in a shipping bag and then sterilized. The sensor may be sterilized by any of the different sterilization methods utilized in the biotechnology, bio-pharmaceutical or medical industries. In an embodiment, the sensor assembly module stores sensor specific information that is unaffected by gamma ray and electron-beam irradiation and monitors such irradiation to be both adequate and not excessive.

Sterilization also can be carried out by way of autoclaving, and the present disclosure addresses risk management, material traceability and post-production or post-manufacturing processes such as factory sensor calibration, sensor usage history and sensor reliability and performance after sensor sterilization by autoclaving, as well as by gamma irradiation. In an embodiment, measures are taken to minimize the risk of incomplete sterilization by way of autoclaving with carefully controlled temperature and pressure, targeting 123° C. and 20-40 psi. An embodiment addresses this with the inclusion of a so-called temperature fuse that is non-resettable.

It is a general aspect of the present disclosure to provide a risk-managed single-use and/or disposable electrical conductivity sensor.

Another aspect is to provide a single-use and/or disposable sensor suitable for one-time use, which may be integrated with other disposable equipment, including bag manifolds, employed in the separation and purification of fluids that are suitable for single-use applications.

An aspect of the present disclosure is to control the cost associated with the construction of electrical conductivity sensors while enhancing performance.

Another aspect of the present disclosure is to provide a sensor having a stored "out-of-box" performance variance value.

Another aspect of the present disclosure is to provide a sensor having the ability to store sensor specific information and that is not affected by gamma ray or electron-beam irradiation techniques.

A further aspect concerns a single-use biopharmaceutical solution processing sensor having usage counter capabilities and with a fluid conduit through which biopharmaceutical solution flows during use of the sensor, an on-sensor memory device, a usage counter associated with the sensor; and the usage counter utilizes motion detection corresponding to solution flow through the fluid conduit as a threshold event to designate a counted sensor use event, whereupon the counted sensor use event is stored on the memory device and accumulates prior or subsequent use events until a maximum use total stored on the memory device is attained.

An additional aspect is a single-use bio-solution sensor having a fluid conduit through which biopharmaceutical solution flows during use of the sensor. Also included is on-sensor memory device and a usage counter associated with the sensor; and said usage counter utilizes pressure detection corresponding to solution flow through the fluid conduit as a threshold event to designate a counted sensor use event, the threshold event is a first pressure spike stored in the on-sensor memory device as a peak pressure along with a corresponding time event feature, the first pressure spike being the greatest pressure detected by the sensor during a given use, whereupon the stored counted sensor use event accumulates with prior or subsequent use events until a maximum use total stored on the memory device is attained.

An added aspect is a single-use bio-solution sensor having gamma radiation exposure reporting capabilities, a fluid conduit through which biopharmaceutical solution flows during use of the sensor, an on-sensor memory device that maintains function under gamma radiation, the on-sensor memory device has an as-manufactured stored pre-gamma radiation threshold voltage and an as-manufactured stored post-gamma radiation threshold voltage greater in magnitude than a pre-gamma threshold radiation voltage, and an on-sensor gamma-responsive component informs the on-sensor memory device of voltage due to gamma radiation exposure, and exposure of the gamma sensor to gamma radiation shifts the voltage in a repeatable manner to indicate the sensor has been sterilized with gamma radiation.

In a further aspect, a single-use bio-solution and/or biopharmaceutical solution sensor having autoclave temperature exposure reporting capabilities includes a fluid conduit through which biopharmaceutical solution flows during use of the sensor, and an on-sensor memory device. Also included is an on-sensor thermal fuse that is readable for transmission of information to the sensor for storage on the memory device, the thermal fuse being set with a threshold autoclave temperature at which the fuse trips and the thermal fuse is electronically interrogatable for fuse tripping prior to its use in solution processing, thereby indicating successful autoclaving.

Another aspect concerns a dockable sensor system combining a multiple-use user interface, a single-use bio-solution processing sensor module and a motion detector. The multiple-use interface has an electronic reception and transmission function and comprising a base having a docking location. The single-use sensor module has a fluid conduit through which biopharmaceutical solution flows during use of the sensor, an on-sensor memory device, and a usage counter associated with the sensor. The usage counter utilizes motion detection by said motion detector of solution flow through the fluid conduit as a threshold event to designate a counted sensor use event, whereupon the counted sensor use event is stored on the memory device and accumulates with prior or subsequent use events until a maximum use total stored on the memory device is attained.

These and other aspects, features, improvements and advantages will be clearly understood through a consideration of the following detailed description.

BRIEF DESCRIPTION OF THE DRAWINGS

FIG. 1 is an illustration of an embodiment of the user interface and of a conductivity sensor assembly that is attached at both ends of a fluid conduit of a fluid transfer system;

FIG. 2 is a cut-away perspective view of the illustrated conductivity sensor assembly of FIG. 1;

FIG. 3 is an exploded perspective view illustration of the FIG. 1 conductivity sensor and the fluid conduit;

FIG. 5b is an elevation view of the conductivity sensor of FIG. 5a;

FIG. 5c is a plan view of the component side of the conductivity sensor of FIG. 3a;

FIG. 7 is an illustration of a sensor with barcodes for storage of sensor specific information;

FIG. 8 is an illustration of a user interface connected to a barcode reader for reading the sensor specific information from the barcodes located on the sensor assembly of FIG. 7;

FIG. 10 is a perspective view of an embodiment, in exploded form, of a single-use flow cell that docks or mates to a reusable interface of the assembly, shown in "undocked" from the non-disposable, reusable interface;

FIG. 11 is an exploded perspective view of the single-use flow cell assembly illustrated in FIG. 10;

FIG. 12 is an electrical schematic associated with the embodiment of FIG. 10 and FIG. 11;

FIG. 13 is a data plot related to a risk management embodiment for a sensor generally in accordance with FIGS. 10, 11 and 12 concerning accelerometer output;

FIG. 16 is a tabulation of data generated after gamma radiation of multiple pressure sensors, same being a FRAM gamma-radiation exposure graph illustrating an explanation for a sensor failure according to data in this Figure.

DETAILED DESCRIPTION OF THE EMBODIMENTS

Figure 4A:
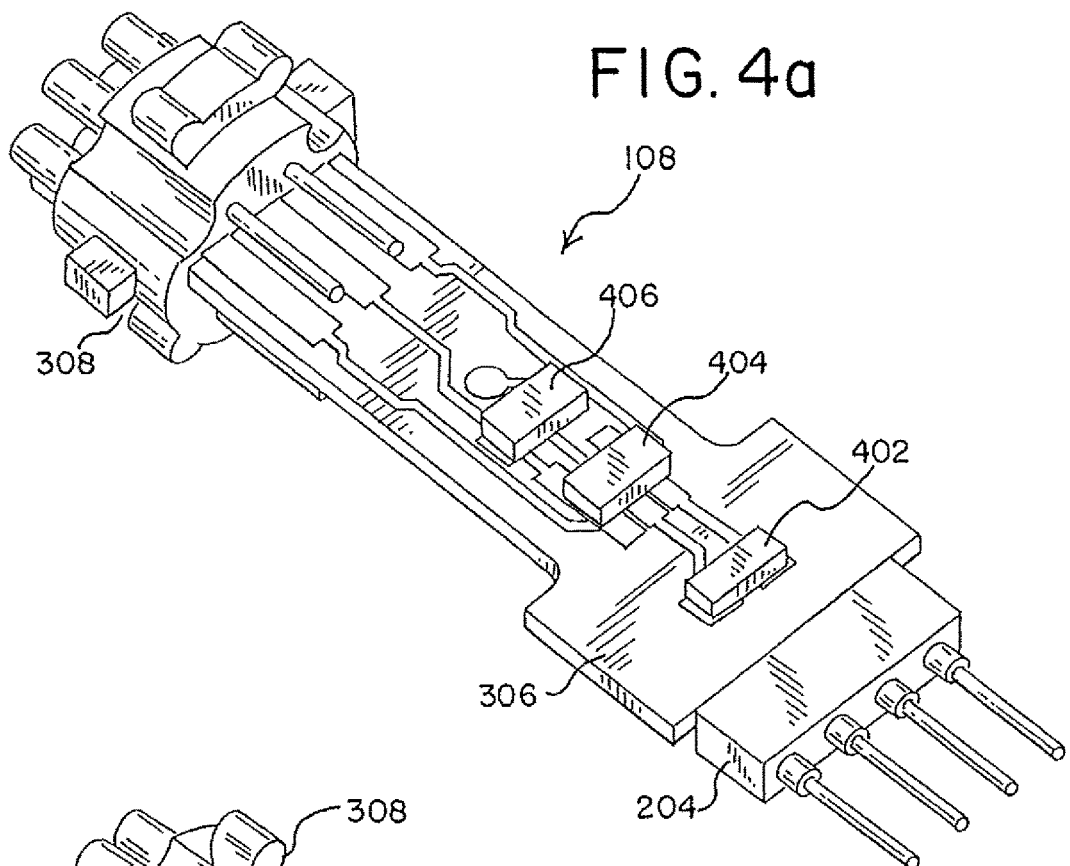
FIG. 4a is a perspective view of the component side of the FIG. 1 conductivity sensor.

As required, detailed embodiments of the present disclosure are set out herein; however, it is to be understood that the disclosed embodiments are merely exemplary of the subject matter, which may be embodied in various forms. Therefore, specific details disclosed herein are not to be interpreted as limiting, but merely as a basis for the claims and as a representative basis for teaching one skilled in the art to variously employ the present subject matter in virtually any appropriate manner.

It will be appreciated that sensors of the present disclosure exhibit what may be understood to be primary sensing functions and secondary sensing functions. These combine to provide optimal processing of valuable biopharmaceutical solutions such as vaccines, monoclonal antibodies and other proteins. The present sensor technology is relevant to both upstream bio-processing and downstream product purification. These sensors are especially suitable for incorporation into disposable polymeric tube manifolds or bag manifolds designed for sterile, closed-loop processing of biopharmaceutical solutions of the type discussed herein and including U.S. Pat. Nos. 6,712,963, 7,052,603 and 7,410,587, and in conjunction with sensor and sensor specifics of U.S. Pat. Nos. 7,857,506, 7,788,047, 7,927,010 and 8,506,162, each of which is incorporated by reference from specific patents. Use is contemplated for either manual or automated normal-flow filtration (NFF), tangential-flow filtration (TFF), single-use centrifugation and preparative liquid chromatography. Sensor use in disposable bioreactor applications for introducing sterile seed solutions and harvesting of cell-derived products, the controlled cell-broth profusion. Same can be associated with bag manifolds and/or tube manifolds.

A Conductivity Sensor Embodiment:

A system designed to measure the conductivity of fluids in a closed fluid system by using a pre-calibrated, single-use in-line electrical conductivity sensor is shown in FIG. 1. The electrical conductivity sensor assembly is generally designated as 100. The assembly 100 is designed to be integrable with a fluid circuit and to be of a single-usage type or disposable. When "single-use" is used herein, same refers to a sensor intended for single-time usage, such as for a set procedure for a maximum duration. These types of sensors may be capable of multiple-time uses but without full confidence. These also are intended to be disposable in an environmentally appropriate manner. Thus the sensors can be single-use and/or disposable.

Contained with the conductive sensor assembly 100 is a short tubular fluid conduit 102, designed for a particular manifold flow rate range of the fluid circuit. Typically, the fluid conduit 102 is tubular and has a diameter between about 3 mm and about 25 mm (about ⅛ inch and about 1 inch). The flow conduit 102 is made of a polymer such as a polyolefin, for example polypropylene, but any other appropriate plastic tubing or material may be substituted. The tubing material should be suitable for engaging and containing the fluid being handled, such as valuable proteins, biotechnical compositions or pharmaceutical solutions. The fluid conduit 102 has molded-in fluid-tight connections 103 and 104, which may consist of Luer, Barb, Triclover, or any connection method suitable to connect the flow conduit 102 in a processing system or fluid circuit, such as the illustrated polymeric tubing 106. A sensing portion or electrical conductivity sensor 108 protrudes through the wall of the conduit in a manner that will be more evident in the subsequent discussion and from the drawings.

Leads such as the illustrated electrical connecting wires 110 connect the conductivity sensor 108 to a conductivity readout device or user interface 112. The user interface, generally designated as 112, is any computer like device that communicates with the sensor 108 and measures conductivity by sending and receiving both digital and analog electrical signals along the leads 110. The user interface 112 has a display 114 to display information, for example, the electrical conductivity reading, the temperature reading, and information stored on the conductivity sensor 108 relating to the calibration, validation and tracking of the sensor.

FIG. 2 is a more detailed view of the conductivity sensor assembly 100. The housing 200 of the assembly 100 preferably is over-molded with a durable material such as a hard polyurethane polymer such as TPE. The durable housing material seals and protects the interior components from moisture and outside contaminants. The sensor 108 can be further protected by a sheath 202 as illustrated.

The fluid conduit 102 traverses the assembly 100 such as along its width as illustrated. Electrodes 204 are in electrical communication with the interior of the fluid conduit 102. In the illustrated embodiment, the fluid conduit is intersected by four electrodes of the conductivity sensor 108. These electrodes 204 can be positioned along the interior of the conduit 102, such as at the middle portion of the conduit. Gold-plated electrodes can be used such as ones that are about 1 mm to about 2 mm in diameter or between about 0.025 inches to 0.05 inches in diameter. Such electrodes preferably are arranged in-line approximately 2 to 2.5 mm (about 0.08 inch to 0.10 inch) apart.

In the illustrated embodiment, the electrode pins 204 are press-fitted into and through four linearly arranged holes in the wall of the fluid conduit 102 and extend into the hollow interior of the fluid conduit 102. Typical protrusion into the conduit is on the order of about 3 mm to about 13 mm (about ⅛ inch to about 0.5 inch). The electrodes 204 are epoxied, cemented or otherwise sealed to the wall of the fluid conduit 102 to prevent leaks or contamination. Additionally, the electrodes 204 are in electrical communication with their respective traces on the sensor 108.

In other embodiments, the electrodes 204 may have only two electrodes or pins rather than four of this illustrated embodiment. In addition, the electrodes may be constructed from other materials, such as stainless steel wire, titanium wire, or any other non-corrosive material. Disposability or recyclability are criteria to be considered in selecting these or any other materials of the device.

FIG. 3 shows a component view of the fluid conduit 102, sensor 108, and sheath 202. The illustrated sheath 202 has a top portion 302 and a bottom portion 304. The illustrated electrodes 204 are press-fitted into and through the wall of the fluid conduit 102 and are connected to the printed circuit board (PCB) 306 of the conductivity sensor 108. The preferred PCB 306 is a double sided PCB with conductive solder traces. Each pin of the electrodes 204 is in direct contact with its respective trace, and each is shown soldered onto the printed circuit board (PCB) 306.

Opposite the electrodes 204, the PCB 306 is wedged between two rows of five pins of a miniature, 8-pin DIN connector 308. These five pins of the DIN connector 308 are in direct contact with the PCB 306 and are soldered to the PCB 306. The three remaining pins of the DIN connector 308 are wired and soldered to the PCB 306. The end of the sensor 108 is capped and sealed by the cap-ring 310. The DIN connector 308 is detachably connected to the user interface 112 by the connecting wires 110. Each pin of the DIN connector 308 is associated with an individual wire of the connecting wires 110.

FIG. 4*a* shows the top view or the component view of the sensor 108. The electrodes 204 are connected to the underside of the PCB 306. A surface-mounted thermistor 402 is in thermal contact with two of the conductivity electrode pins when four are provided. A second, important function of the thermistor is to act as a pull-up resistor for the non-volatile memory chip, thereby assuring proper functioning of the memory device. The thermistor 402 is used to monitor the temperature of the solution in the fluid conduit 102, via thermal conductance, such being transmitted to the user interface 112. The user interface 112 reports the solution temperature data and utilizes the temperature data to correct or normalize the solution electrical conductivity reading.

A sensor-embedded non-volatile memory chip or an EEPROM 404 is mounted on the surface of the PCB 304. The non-volatile memory chip or EEPROM 404 is used to store sensor-specific information. This information can be called up, displayed and printed out, on demand, by the user interface 112.

Figure 4B:
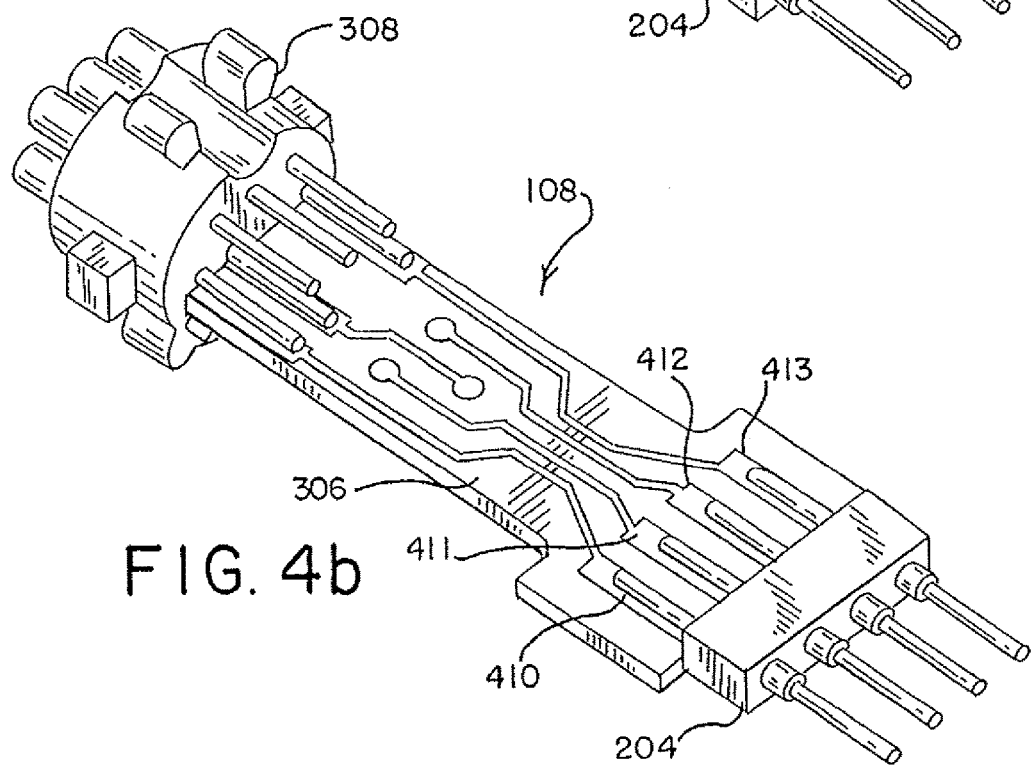
FIG. 4b is a perspective view of the underside of the illustrated conductivity sensor.

The PCB 306 also contains a surface-mounted capacitor 406 that is visible in FIG. 4*a*. FIG. 4*b* is an illustration of the underside of the PCB 306 in the four electrode embodiment. The electrodes 204 are soldered to their respective traces 410, 411, 412, and 413. FIG. 4*b* also further demonstrates the wedging of the PCB 306 between the pins of the DIN connector 308.

Figure 5C:
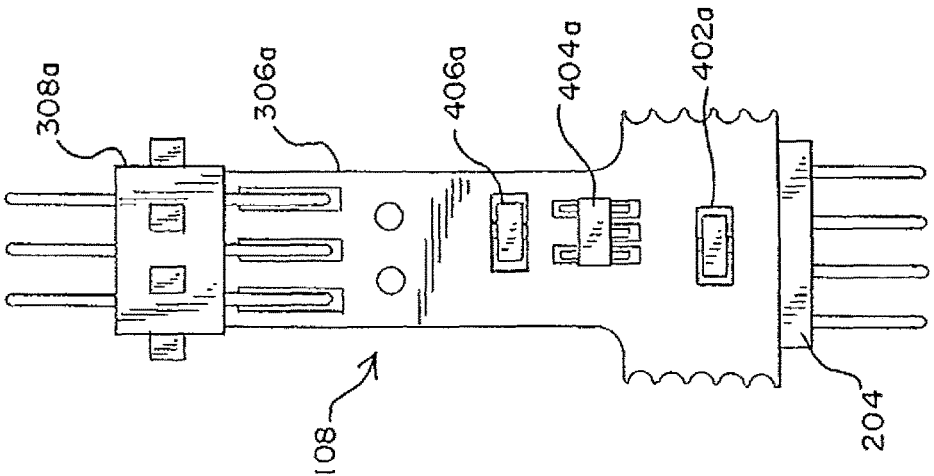
Figure 5B:
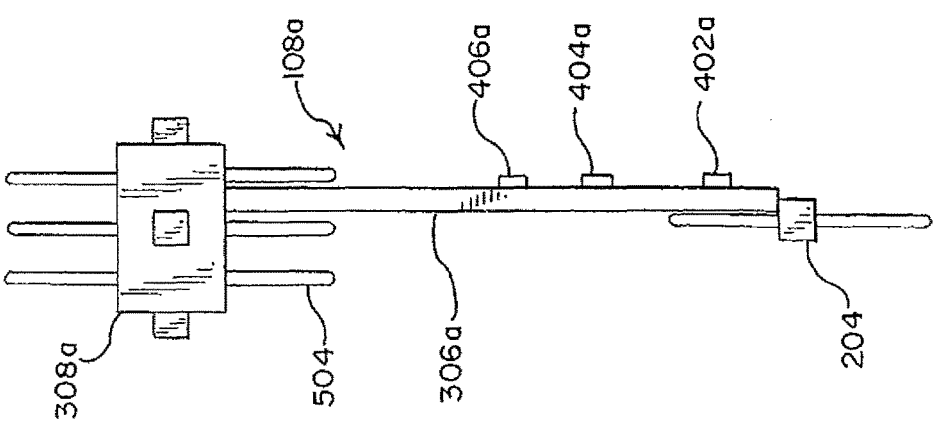
Figure 5A:
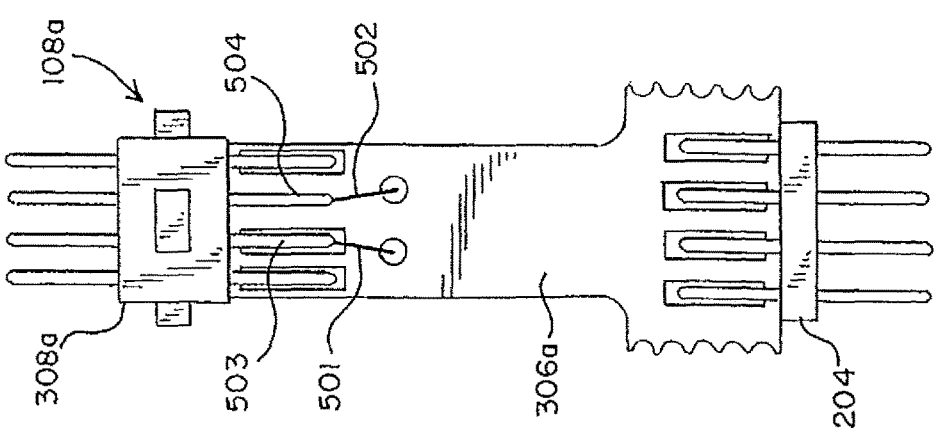
FIG. 5a is a plan view of the underside of another embodiment of a conductivity sensor.

FIG. 5*a* is a plan view of the underside of a PCB 306*a* of the conductivity sensor 108*a*. Soldered connections 501 and 502 to the PCB connect two pins 503, 504 of the 8-pin DIN connector 308*a* that are not in direct contact.

FIG. 5*b* is an elevation view of the conductivity sensor 108*a*. FIG. 5*b* also shows how the PCB is sandwiched between the pins of the DIN connector. The low profiles of the capacitor 406*a*, non-volatile memory chip 404*a* and the thermistor 402*a* are also evident in FIG. 5*b*.

FIG. 5*c* is a plan view of the conductivity sensor 108*a* that is shown in FIG. 5*a* and FIG. 5*b*.

Figure 6:
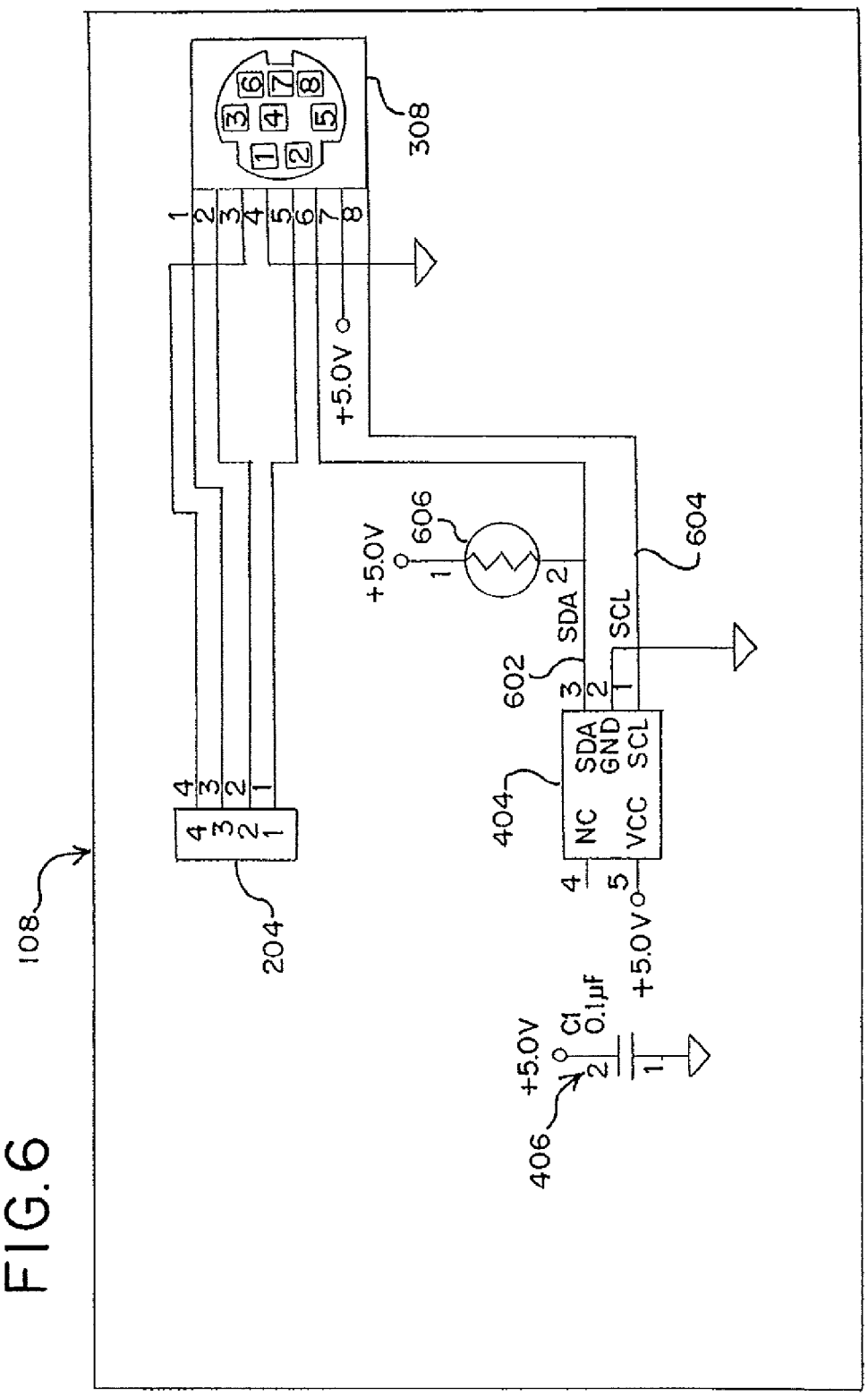
FIG. 6 is a schematic circuit diagram of the FIG. 1 conductivity sensor.

FIG. 6 is an electric circuit diagram illustrating the various connections of the sensor 108 in this embodiment that is illustrated. Four connections from the 8-Pin DIN connector 308 are connected to the four pins of the electrode 204. One pin of the DIN connector 308 provides a 5.0 Volt power supply to the capacitor 406, the non-volatile memory chip (or EEPROM) 404, and a bi-directional serial data line 602. One pin of the DIN connector 308 provides the ground for the capacitor 406 and the non-volatile memory chip (or EEPROM) 404.

The non-volatile memory chip (or EEPROM) 404 uses the bi-direction serial data line 602 and a serial clock line 604 to communicate with the user interface. Different non-volatile memory chips or EEPROMS have different protocols, which are known in the art. In this embodiment, the serial data and serial clock lines allow a user interface 112 or a calibration device to read, erase, and write data to the non-volatile memory chip 404. The serial data line 602 is an open drain terminal. Therefore, the serial data line requires a pull-up resistor 606 connected to the voltage source coming from the DIN connector 308. In this embodiment, the thermistor 402 also serves as the pull-up resistor 606.

The sensor-specific information is electronically entered into the non-volatile memory chip 404 during factory calibration of the conductivity sensor 108. The sensor-specific information may include the following: Cell Constant (K), Temperature Offset, the unique Device ID, and the Calibration Date, the production lot number of the sensor, the production date of the sensor, the type of fluid used for calibration, the actual temperature of the fluid used, and "out-of-box" sensor performance value.

Sensor-Specific Characteristics and Calibration:

During production, small differentiations in the electrodes 104, the respective angles of the electrodes, and the gaps between the individual electrodes will result in different electrical conductivity readings for each sensor produced. These differences can significantly affect accuracy. These differences are successfully addressed by having each sensor normalized or calibrated as a part of its manufacturing procedure.

In the illustrated example, each conductivity sensor 108 is calibrated using certified 0.100 molar KCl (potassium chloride) solution maintained at 25.0° C. The conductance, which is dependent on the cell geometry and the solution resistivity, is determined by measuring the voltage drop across the electrodes. The measured conductance together with known solution electrical conductivity allows the calculation of the sensor-specific Cell Constant (K). The Cell Constant (K) is determined by the following equation:

$$[\text{Solution Conductivity},(S/cm)]/[\text{Conductance}(S)] = [\text{Cell Constant}, K, (cm^{-1})]$$

The sensor-specific Cell Constant (K) is then stored in the non-volatile memory 404 of the conductivity sensor 108.

For example, the solution conductivity for a 0.100 molar KCl solution is known to be 12,850 µS (or 0.01285 S) at 25.0° C. The typical measured conductance for a 0.100 molar KCl solution using a sensor with a ⅛ inch Luer conductivity cell with a 0.10 inch electrode separation is 0.0379 Siemens. Using the equation above, the corresponding Cell Constant (K) for the particular disposable sensor of this illustration is calculated to be 0.339 $cm^{-1}$.

Once the Cell Constant (K) is calculated it is stored on the sensor. The user interface will recall the Cell Constant (K) from the sensor. When undergoing normal operations, the user interface 112 measures the conductance in Siemens of the solution flowing through the fluid conduit 102 by passing a current through the electrodes 204 and measuring the current across the two inner electrodes 204. The user interface 112 will then use the Cell Constant (K) for this particular disposable sensor to determine the electrical conductivity of the solution flowing through the fluid conduit. The user interface calculates the solution's conductivity by multiplying the measured conductance by the Cell Constant (K), as demonstrated in the following equation:

$$[\text{Cell Constant}, K, (cm^{-1})] \times [\text{Conductance}(S)] = [\text{Solution Conductivity},(S/cm)]$$

The sensor, once calibrated, provides a linear response for NIST traceable standard solutions ranging from 1 to 200,000 µS.

The temperature of a solution will also affect its electrical conductivity. As a result, the sensor must also measure and account for the temperature of the solution to achieve an accurate conductivity measurement. Ordinarily, un-calibrated thermistors will have a variance of ±5% between their measured reading and the actual temperature. A calibrated thermistor may achieve a variance of ±1% or less.

In this regard, a sensor-specific Temperature Offset is calibrated at the factory. To determine the Temperature Offset, temperature readings are made while a 25.0° C. KCl solution is pumped through the fluid conduit and over the electrodes. A comparison is then made between the temperature reading of the un-calibrated thermistor on the sensor (Tsen) with that of a NIST-traceable thermometer or thermistor (Tref). The difference between the two readings is the Temperature Offset (Tref−Tsen=TempOffset). The Temperature Offset may have either a positive or a negative value. The sensor-specific Temperature Offset is then stored in the non-volatile memory on the sensor.

Each sensor has an "out-of-box" performance variance value which is also stored on the sensor, typically in the non-volatile memory chip. This "out-of-box" value is a statistically derived performance variance (measured in 0.100 molar KCl at 23.0° C.) that represents the maximum measurement error for that specific sensor within a 98% confidence limit. The statistically derived variance value is based on the performance analysis of all calibrated sensors within a production run, typically of between about 100 and about 500 sensor assemblies. The factory determined performance variance represents a predictive, "out-of-box" sensor performance level. This statistical treatment is analogous to and representative of a sensor validation procedure. Factory pre-validated electrical conductivity sensors are thereby provided. The meaning of "pre-validated" is further illustrated herein, including as follows.

In the illustrated embodiment, each conductivity sensor undergoes two factory measurements. The first measurement involves sensor calibration and determination of the specific Cell Constant (i.e. response factor) using a 0.100 molar KCl solution at 25.0° C. as described herein. In another separate and distinct measurement with 0.100 molar KCl solution at 25.0° C., the solution electrical conductivity is experimentally determined using the pre-calibrated sensor. When taking into account the experimentally derived solution conductivities for all pre-calibrated sensors, the mean conductivity value closely centers around the theoretical value of 12,850 µS with a 3-sigma standard deviation of +/−190 µS or +/−1.5% An operator may access this information via the user interface 112 or Conductivity Monitor.

In addition to the calibration information, such as the Cell Constant (K) and the Temperature Offset, the sensor-specific Device ID, Calibration Date, and statistical information are stored in the non-volatile memory. The Device ID is stored as a string of numbers, for example: nn-ss-xxxx-mmyy. In this example, the variables represent the sensor lot number (nn), fluid conduit size (ss), the device serial number (xxxx) and the manufacturing date by month and year (mmyy). For example, sensor containing the Device ID of 02-02-0122-1105 means that this sensor was the $122^{nd}$ sensor made in lot 02 of conduit size 02 (a fluid conduit with a diameter of ⅜" or 9.5 mm having a barb connector), manufactured in November of 2005. In this illustration, the sensor-specific Calibration Date or the date on which the sensor was calibrated using 0.100 molar KCl solution at 25.0° C. is also stored in the sensor's non-volatile memory as a separate data entry.

Additionally, statistical information or statistical data about the entire lot may also be stored in the non-volatile memory. For example, the average cell constant for lot 122 may be stored in the non-volatile memory of each sensor in lot 122. The standard deviation for cell constants for each lot may also be stored (i.e. "out-of-box" variance value) in the non-volatile memory of each sensor produced in that lot. This allows the user to determine whether a particular sensor is within the statistical range to achieve the proper margin of error for a specific experiment or bio-processing operation. As those skilled in the art will appreciate, other known statistical methods may be utilized, the results of which may be stored in the non-volatile memory on the sensing device.

In addition to storing the Cell Constant (K), Temperature Offset, Device ID, the Calibration Date, and other information in the non-volatile memory on the sensor, a summary of this information may be printed on the outside of the sensor. This information may be consulted by the user, used to later re-calibrate the sensor, and allows the user to input the printed information directly into the user interface. Some or all the information which is stored in non-volatile memory may also be printed or etched on to the sensor in the form of a barcode or label containing a barcode.

Sensor Barcode Embodiment:

As shown in FIG. 7, an etched or printed label 702 containing one or more barcodes 702a and 702b is affixed to the exterior housing 701 of the sensor assembly 700. The sensor assembly has an 8-Pin DIN connector 704 which operates as described above. The sensor assembly also has a fluid conduit 706, designed for receiving fluids at particular manifold flow rate range of the fluid circuit. The barcodes encode some or all of the sensor-specific information contained in the sensor memory device, EEPROM or memory chip. The barcodes are not affected by gamma or electron-beam irradiation. Thus, if the sensor memory is erased, becomes non-function, or is destroyed, the sensor-specific information is recoverable from the barcodes affixed to the sensor housing 701 by using a barcode reader or scanner.

As shown in FIG. 8, a handheld optical barcode scanner 800 is hooked up to a digital I/O port of the user interface device with monitor 114. Additionally, the sensor 700 is also connected to the user interface 112 via the 8-pin DIN serial port 704 as described above.

The user interface 112 has software for connecting with a barcode scanner 800 and decoding the barcode label 702 on the sensor 700 and memory for storing the information read from the barcode. By scanning the barcode with the barcode reader 800, the sensor specific information is read and stored by the user interface 112. The sensor specific information is then accessible to the user interface 112 such that the user interface 112 may use that information to calculate the sensor-specific response. When fluid or solution is passed through the fluid conduit 706, the user interface 112 collects analog measurements from the sensor. The user interface 112 then uses this raw analog data along with the sensor-specific calibration factor (i.e. the Cell Constant) and the temperature offset factor (TempOffset) obtained from the barcodes to calculate the sensor-specific response (i.e. the actual conductivity of the fluid). As shown in FIG. 7 the calibration factor is printed on the label as "CF 0.182" and the temperature offset is printed as "TO −0.6."

Other types barcodes or marking conventions may be used other than the linear barcodes as shown in FIG. 7. For example multidimensional barcodes, 2D barcodes or matrix codes may be used in place of the linear barcodes. The barcodes may also be affixed or etched on portions other than the sensor housing, such as on the fluid conduit 706 or the shipping bag or container.

An important sensor design consideration is accessibility of the sensor analog circuitry (for example, the circuit connected to the thermistor and electrodes) by the user interface 112, even when the sensor memory device is non-functional or destroyed. Experimentation by the applicant suggests that the analog circuitry of the sensor embodiment as depicted in FIGS. 2-6 is unaffected by gamma or electron-beam irradiation. Thus, separation of analog circuits and digital circuits (i.e. circuits to the memory device) of the sensor is desirable. By separating the analog and digital circuits, the analog circuits maintain functionality and can provide the user-interface 112 with raw data.

As gamma or electron-beam irradiation renders the memory chip or EEPROM non-functional, it is contemplated that sensor units may be manufactured without memory chip. In these embodiments, the analog components are manufactured and assembled into sensors. The sensors are validated and the sensor specific information is then printed on the sensors or shipping bags in print or barcode form. The sensors are then placed in shipping bags or other suitable containers, irradiated via gamma rays or electron-beam, and then delivered to the user. The sensor specific information is entered into the user-interface 112 either by a barcode scanner 800 as shown in FIG. 8, or manually by the user. This embodiment saves the costs associated with including the memory chip with the sensor.

Figure 9:
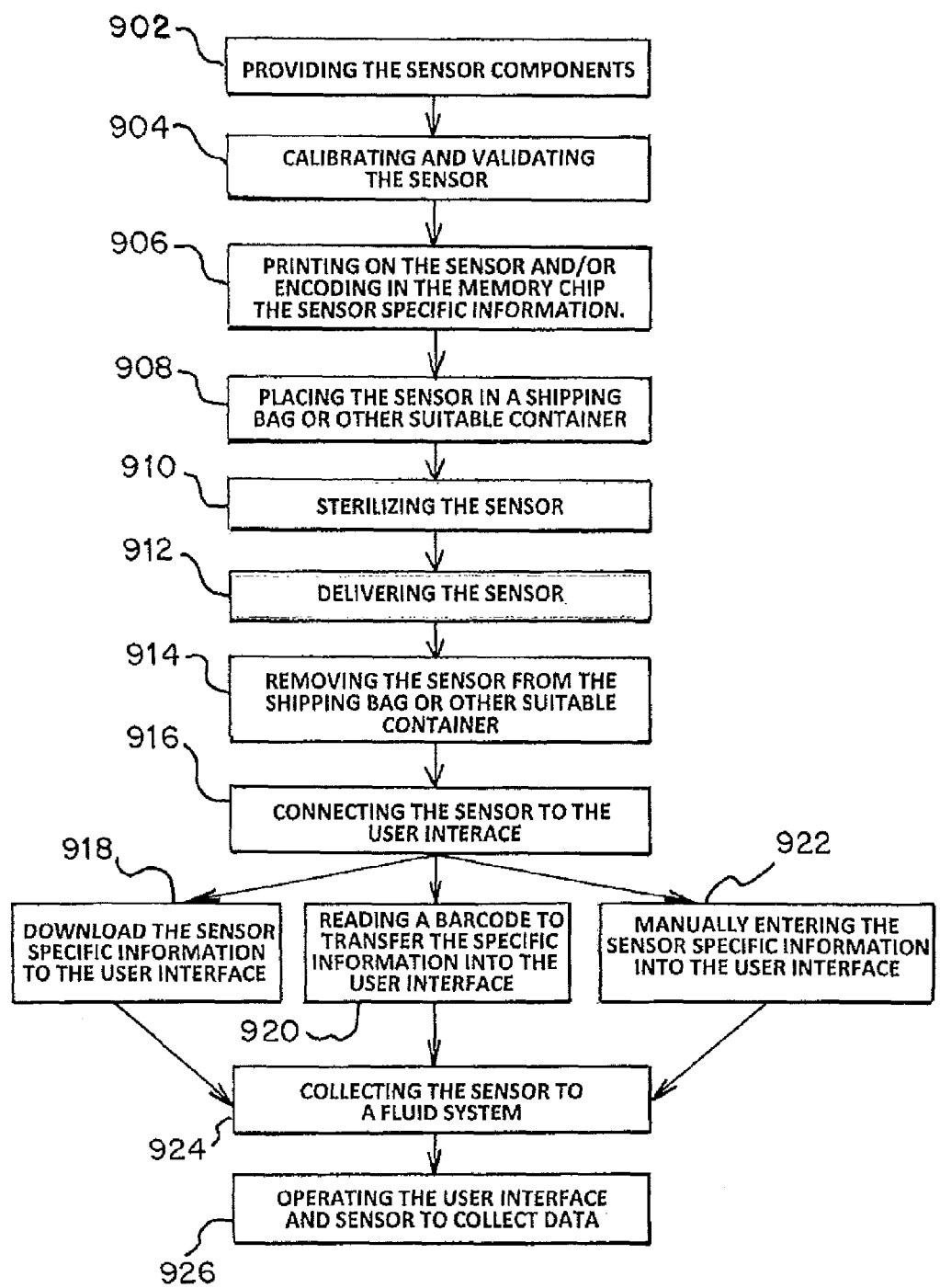
FIG. 9 is a flowchart illustrating the lifecycle of a sensor of FIG. 7.

A method of preparing a sensor for use in bio-pharmaceutical industry is illustrated in terms of this barcode embodiment and is generally applicable to other embodiments. As shown in FIG. 9, the sensors are first manufactured. The sensors may be manufactured to include analog and/or digital circuits. The analog circuits may be used for data collection purposes, while the digital circuits may be used to store sensor specific information. The sensors are then calibrated and validated using the techniques mentioned above and/or those known in the art. The sensor specific information obtained during the calibration and validation steps is then stamped or printed on the sensor in the form of a barcode or other readable form. If the sensor includes a memory chip, the sensor specific information is also stored on the memory chip.

The sensor is then placed in a shipping bag or other container, at 908. The container and/or the sensor are then sterilized by autoclaving, time-limited exposure to an ethylene oxide gas, gamma ray irradiation, electron-beam irradiation, or by any other method known in the art, at 910. The sensor and container are then stored until they are deliver to the user, at 912.

The user then removes the sensor from the shipping bag or other container, at 914. The user then connects the sensor to the user interface, at 916. If the sensor includes a memory chip containing sensor specific information, the user interface downloads that information, at 918. Otherwise, the user uses a barcode scanner connected to the user interface to read and enter the information into the user interface, at 920 or enters the sensor specific information found on the label, at 922. Either before or after entering the sensor specific information, the sensor is connected to the in-line system, closed-circuit or fluid transfer system, at 924. The user interface and the sensor are then used to collect data, at 926, such as electrical conductivity, from the fluid passing through the system. Because the sensors are designed to be single use and/or disposable, at the end of its life cycles the sensors may be destroyed, thrown out, or recycled.

Modular Sensor Re-Use Risk Management:

In conjunction with the present disclosure, single-use technology risk management is applied, including risk assessment and mitigation, particularly in the context of good manufacturing practices that may be mandated in biopharmaceutical handling and production. This is illustrated in connection with a multiple-use user interface 915 and a single-use sensor assembly module 917. These two main components have a releasable assembly characteristic, such as the illustrated docking arrangement whereby a docking face 937 of the single-use sensor module securely but releasably docks at a docking location 931 of the multiple use user interface. Thus, a fresh and sterile single-use module 917 is secured to the interface 915 prior to use (and typically in a sterile environment). After completion of solution processing through a manifold system as generally discussed herein, the module 917 is easily separated from the interface 915, allowing for re-use of the interface with a fresh module 917.

Intentional or accidental re-use of single-use sensors and manifolds in good manufacturing practices applications can be compromised by excessive, long-term use of single-use sensors. Non-good manufacturing practices applications can include accidental or intentional re-use of single-use sensors and manifolds represents a significant contamination risk potential. The present disclosure provides usage control for limiting the risk of contamination and/or potential component failure. Included is a time-restricted, active usage limit for single-use sensors. As an example, critical downstream good manufacturing practices purification applications can call for sensor usage to not exceed 50 hours, which can vary depending upon criteria of a user, such as a user's metrology department. Upstream bioreactor applications may tolerate less strict usage limitations particularly where sterilizing filters (such as of the NFF type) are incorporated with back-pressure monitoring.

A sensor usage counter is a risk management approach that provides a time and performance history for a specific sensor from installation to de-commissioning of the sensor. The sensor usage counter is initialized by a threshold event, which can be visualized when connected to a monitor. For example, when the sensor is a pressure sensor, the threshold event will occur when a pre-selected pressure level has been exceeded, for example, 1 psi of pressure. This threshold event is further characterized by a pre-selected time interval, for example, five minutes. In this case, the time interval will be counted as a sensor "use" only when the threshold event has occurred for five minutes or longer. Accordingly, sensor use can be equated to achieving a particular parameter value for a given length of time. In an embodiment, the specific sensor usage and associated time intervals are stored in the on-sensor memory device.

In a further usage-counter embodiment, the total accumulated sensor usage time also can be pre-selected, for example, 100 hours. The elapsed usage time and/or the remaining usage time typically are updated at regular intervals, and when the sensor is connected to a monitor, such is visible by the monitor. Such data are stored in the on-sensor memory. The remaining time will be displayed on the monitor when provided, and an alarm will be signaled when the pre-selected total usage time has been obtained. At this point, the sensor usage counter, when provided with input provisions for disabling the sensor, continued sensor usage will be prevented. Alternatively, an override feature can be provided that allows continued use of the sensor, such as by authorized personnel having a password-protected opportunity to intervene and set limits on sensor usage.

A more automated sensor usage counter can be provided through the inclusion of an electronic motion detection device responsive to pulsating pump action (such as of peristaltic or piston pumps) resulting in a more autonomously functioning sensor usage counter. An example of a suitable electronic motion detection device is a 3-axis accelerometer chip manufactured by Freescale, for example part number MMA8450Q. Typically this will be accompanied by supporting electronic circuitry capable of operating and monitoring the motion detection device, such as illustrated in FIG. 12. Such a device is capable of detecting small, induced sensor motions in three dimensions with high resolution, and thus can be utilized as a general marker capable of detecting beginning and end of the usage cycle of a sensor, manifold or the like during processing of biopharmaceutical solutions. Same can be utilized as a general on/off event marker.

Positioning an accelerometer located in the electronics module of interface 915, when the single-use sensor and flow cell 917 is attached to it, such as at docking station 931 of the interface, results in the accelerometer being sensitive to pulses such as peristaltic pump vibrations of fluid moving through tubular fluid conduit 929. These vibrations are analyzed by the system software for frequency content and amplitude. These signals are indications that the sensor is being used. Signals can be transmitted to a processing unit or monitor (not shown) by way of a lead assembly 933. Based on the accelerometer data (and, when available, thermistor data as noted elsewhere herein), the software in the system writes to the sensor memory and marks a sensor "used" event or count. The system may also limit the total run time that a sensor can be active to address the possibility that the sensor is used after a certain level of fluid sample exposure.

During pumping through a single-use sensor or manifold, pulses are generated, and the present disclosure operates to detect the resulting sensor vibration, thereby indicating the start of usage of the sensor, manifold or the like. When vibration of this component or system ceases, the end of the sensor usage campaign is indicated. This has the capability of providing an on/off event detector as a useful indicator for generalized, autonomous sensor usage counter-functioning that does not require user or operator input. Same is independent of the level or nature of the sensor signal parameter, such as pressure, temperature, conductivity or turbidity. This usage information is automatically stored in the on-sensor memory, for example, a FRAM memory device 925.

The accelerometer can take the form of a small-area printed circuit board accelerometer, attached to outside of a single-use analytical flow through sensor as generally discussed herein. In a particular accelerator embodiment, its circuitry is integrated into the printed circuit board of the sensor, such as by the circuitry detailed in FIG. 12. For example, FIG. 10 shows such an internal accelerometer 913 positioned on the non-disposable interface module 915 onto which the single-use flow cell assembly 917 is mounted in a secure and yet removable manner to facilitate replacement of a sensor beyond its designated useful life with a fresh sensor and typically a fresh complete flow cell assembly 917. Flow cell assembly 917 typically includes a circuit board 935 and electrodes 921. Four electrodes are shown, with two typically providing the excitation levels and the other two being sense lines used to determine conductivity of the solution, when the device is an electrical conductivity sensor.

For constant-pressure solution delivery systems where pressure pulses are generally absent or at least not readily detectable, the present disclosure provides an alternative to the accelerometer-initiated sensor usage counter. This alternative approach utilizes a self-heating thermistor installed as a part of the analytical flow-through sensor. This approach can provide a simple on/off usage-countersignal. When such a heated thermistor is exposed to air, same will assume a different resistance value (in ohms) when compared with its exposure to a flowing liquid, which effectively cools the thermistor. Detection of the flowing liquid will initiate the sensor-usage counter while exposure to a non-flowing fluid stream, or to air, will stop the usage counter.

In FIG. 11, such a thermistor 927 is illustrated protruding into the flow cell, resulting in direct contact with the sample fluid. The thermistor 927 can achieve two functions. The thermistor can be used to measure the temperature of the fluid in connection with the compensation discussed elsewhere herein for electrical conductivity measurement deviations due to temperature effects. This thermistor can also periodically be given a small amount of energy, such as imparting a short current spike. Such energy spike causes a short-term increase in the temperature of the thermistor. The decay time of the temperature following the energy spike is used to determine if the sensor is filled with fluid and to measure the fluid flow rate. These two measurements are indicators that the sensor is being used, thus registering a "use count."

Figure 14:
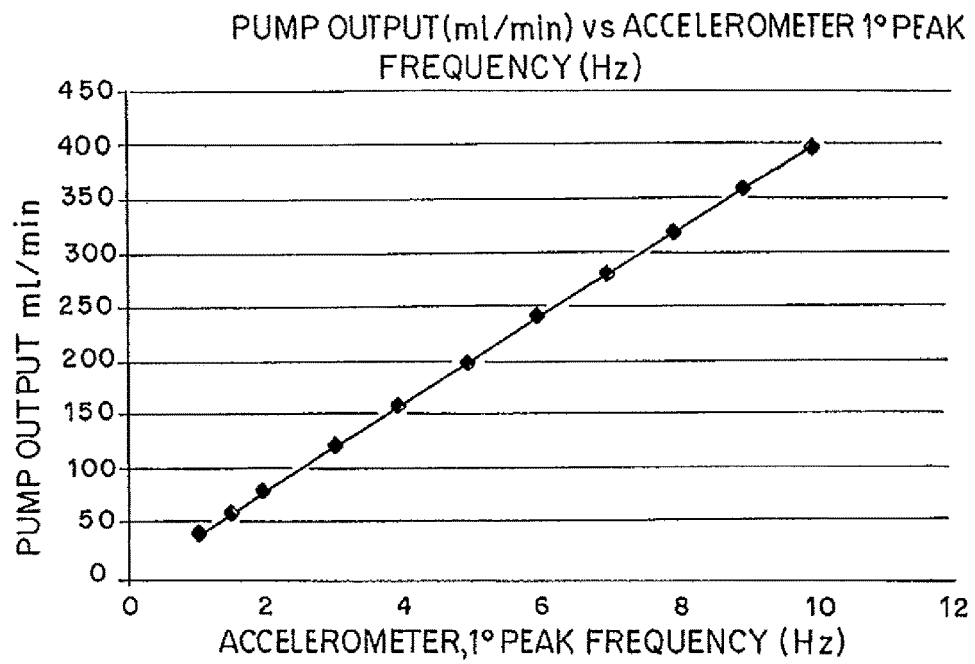
FIG. 14 notes test results with a functional accelerometer embodiment of the sensor of FIGS. 10, 11 and 12.

The sensor usage counter can incorporate a flow meter function. In such an approach, it is appreciated that the auto-correlated output of the accelerometer chip 913 discussed hereinabove generates a peak train whose frequency (in Hz) is identical with the rotational pulse frequency. This is illustrated in FIG. 13, which plots relative peak height versus time of the pump (e.g., peristaltic or piston). Typical test results (see FIG. 14) obtained with a functional accelerometer as attached to the analytical flow-through sensor show that the measured frequency of the peak train is related to the fluid pump output. As generally noted above, the accelerometer is capable of distinguishing between non-compressible test fluids (e.g., tap water) and compressible fluids (e.g., air). For a given pump rate, the accelerometer output differential between water and air (using these examples) is 3.5 orders of magnitude. This sizeable magnitude difference means that the device can readily detect larger air pockets that may have been transferred from an empty reagent bag, thereby indicating the end of a reagent dispensing cycle. This can be applied in connection with a use-counting function.

The magnitude of the accelerometer output signal is affected by the mechanical attachment of the accelerometer and sensor assembly. The greatest output signal is obtained with a freely suspended sensor and manifold assembly. However, a rigidly attached sensor will result in a lower but stable accelerometer output. For improved flow rate accuracy, a peak-to-peak integration of the accelerometer output signal typically is preferred over peak height measurements.

When desired, and in certain situations, the sensor motion detection device of the automated sensor storage usage counter noted hereinabove is used in conjunction with specific sensor output in order to provide a second level output confirmation of the sensor motion detection device. For example, the output of the sensor motion detector device can be electronically compared with the output of a pressure-sensing element co-residing on the sensor printed circuit board and in contact with a tube conduit through which the biopharmaceutical solutions flow.

With this approach, any solution being pumped through a sensor, tube or manifold—such as with a peristaltic pump or similar device—will set up sensor vibration as detected by the motion detection device as well as co-detected pressure pulses detected by the pressure sensor which is in physical contact with the fluid conduit defined by the tube manifold or other system or device. The pulse frequency and/or the signal magnitude can be used for usage confirmation for a device or component being monitored.

Furthermore, the on-sensor stored information provides the basis for a sensor, manifold or other device usage "diary" that collects and stores events. For example, on/off events that are triggered by the starting and stopping of the pump action are stored as on/off events. When desired, the event data will be stored with time of day and calendar stamps, together with pressure, temperature or any other relevant sensor output information. Or, if desired, only pump on/off event data sets can be stored, thereby providing a long-term contextual sensor, manifold or other device data set. This can be useful in maximizing on-sensor data storage.

Autoclave Temperature Threshold Indicator:

A common practice in the bio-processing industry is to have devices in contact with valuable fluids sterilized prior to use. Two major sterilization approaches are autoclaving and gamma-irradiation, and each type of sterilization is suitable for single-use sensors and manifolds prior to their use in accordance with the present disclosure. Considering autoclaving, same is typically carried out at approximately 123° C. and at 20-40 psi, requiring carefully controlled temperature and pressure during autoclaving. Also important is a post-autoclave drying cycle requiring near vacuum conditions for rapid removal of any residual steam condensate. Incomplete or slow removal of the steam condensate can cause significant corrosion of electronic components on the sensor, creating a risk of compromising sensor functionality and performance. It has been known to use sterilizing air filter cartridges at open ends of a manifold in order to speed up sensor drying by providing large drying surface areas, which can increase expense.

With the approach of this particular embodiment of risk management according to the present disclosure, the risk of incomplete sterilization of a single-use sensor and manifold is addressed by incorporating a passive, normally closed, non-resettable temperature or thermal fuse 923 (FIG. 11). This is incorporated as an integral part of the analytical sensor circuitry illustrated in FIGS. 10, 11 and 12. For example, the thermal fuse can be set at a threshold of 123° C. The status (open or closed) of the thermal fuse 923 can be digitally interrogated during post-autoclave sensor power up. If the sensor monitor detects an open fuse circuit, the sensor has been sterilized at 123° C. If the autoclave did not obtain this sterilization temperature, the circuit will be closed, indicating a non-sterile sensor condition. When the thermal fuse is opened, this can be read by the system as a decrease in the current sourced by the SDA pin shown in FIG. 12, for example. This is used by the system to detect that the sensor has been autoclaved.

Gamma Irradiation Threshold Indicator Risk Management:

Another often-used sterilization protocol relies upon gamma-irradiation, in respect of which problems arise with incomplete sterilization due to lower gamma-radiation exposure levels. Problems also arise with excessive gamma-radiation levels that can cause breakdown of plastic polymer sensor materials, potentially resulting in increased levels of leachable and extractable and associated undesirables, leading to concerns of contamination of valuable biopharmaceutical products. Nevertheless, gamma-based sterilization is desirable because of its avoidance of environmental stresses and conditions encountered during autoclave sterilization.

Basically, sterilization by gamma-irradiation provides a time-controlled radiation exposure level in the 25 to 45 kGy range that is effective and sufficient to kill any potentially contaminating microorganisms that may have survived pre-radiation cleaning procedures. Typically after such cleaning procedures, products are bagged and sealed and then subjected to gamma-radiation exposure, providing a packaged product that effectively maintains sterility for many weeks. At the time of use, the sterile product is removed from its packaging in an aseptic environment just prior to installation and use.

By proceeding in accordance with this aspect of the present disclosure, it is possible to determine and document gamma exposure level prior to distribution, commissioning, or use of the sensors, sensor manifolds, tube manifolds, bag manifolds or other devices or components of the present disclosure. The present gamma-radiation threshold indicator is illustrated by the circuit suitable for present use that is provided in FIG. 12. It is known that gamma-irradiation affects the performance of bipolar transistors. Ionizing gamma radiation causes the base current in bipolar transistors to increase, due to the presence of net positive charges in the oxides covering the sensitive device area and increases in surface recombination velocity. When exposed to gamma radiation detected by gamma sensor 919, the component F1 in FIG. 12 functions as a non-resettable gamma-radiation indicator. The measured and stored difference in pre-gamma and post-gamma threshold voltage is effectively used as a qualitative (yes/no) post-gamma-radiation indicator.

With more particular reference to FIG. 12, bipolar transistor Q1 has both its base and emitter tied to the system electronics by way of connector P2. Using pins 1 and 2, the system scans the Q1 base current and measures the Q1 collector voltage. This measurement is made during manufacture, and the relationship between current gain and Q1 base voltage is stored in the sensor memory U1. If the sensor has been exposed to gamma radiation, the relationship between current gain and base voltage will shift in a repeatable way. This is used by the system firmware to detect a sensor that has been sterilized with gamma radiation.

As discussed hereinabove, by proceeding as presently disclosed, gamma irradiation of sensors and of tube manifolds is a cost-effective alternative to autoclaving. In addition to degradation of polymer materials with excessive gamma radiation (for example, in excess of 45 kGy), gamma irradiation of silicon-based memory chips will destroy all memory content, resulting in non-functional memory. According to testing, sensor polymer material and electronic components should remain functional after exposure to from between about 25 and about 45 kGy. FRAM chips are gamma stable up to 45 kGy; however, chip supply voltage should be raised to 5.5 volts for such a chip to remain functional at higher gamma irradiation levels. Same is illustrated, for example, in FIG. 15, discussed in greater detail herein. Sensor response after gamma irradiation data are reported in FIG. 16.

Regarding FIG. 16, Applied Air Pressure signifies a calibration test pressure (e.g., 30 psi) or the stress test pressure (90 psi). CF1 and CF2 are two on-sensor stored calibration factors that define the pressure/response curve for a specific sensor. Along with the PZ value, these are the calibration parameters for a three-point calibration for the pressure sensor with which these data were generated. Air pressure from a pressurized air tank was supplied to a set of dead-ended pressure sensors where the PZ value was determined at zero psi applied pressure, CF1 is the calibration factor for a 6.00 psi (10% FS) applied air pressure, and CF2 is the calibration factor for 54 psi (90% FS) applied pressure, these three, on FRAM-stored parameters, defined the sensor-specific response curve from 0 psi to 60 psi.

Figure 15:
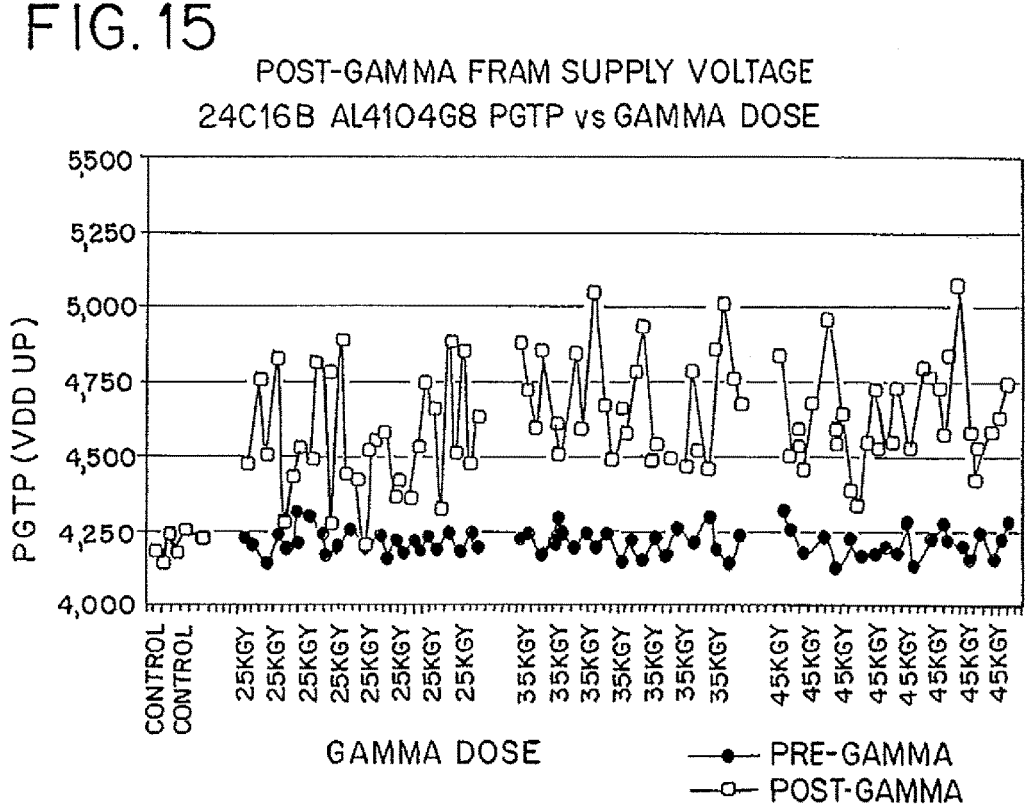
FIG. 15 is a plot of gamma-radiation dose data versus voltage, in the context of a FRAM device.

The present approach of this embodiment makes use of FRAM devices which have been determined to survive gamma-radiation levels in excess of 45 kGy. This is illustrated, for example, in FIG. 15. Gamma irradiation of the FRAM memory devices is accompanied by an increase in the threshold voltage of the FRAM. The average pre-gamma threshold voltage is 4.25 (+/−0.050) volts, whereas the average post-gamma irradiation threshold voltage is measured at 4.75 (+/−0.250) volts. This difference can be used as a qualitative (yes/no) gamma irradiation indicator that the sensor or the like had been subjected to gamma irradiation. This is an example illustrated in FIG. 15, showing a distinct difference in voltage measurement between the pre-gamma data and the post-gamma data plot.

This difference between pre- and post-gamma irradiation threshold levels can be used as a quantitative gamma-level meter. For example, the sensors or the like being evaluated are exposed to a controlled (i.e., known, certified and published) gamma-radiation level. By this approach, the published gamma exposure data, together with the corresponding measurement of the average post-gamma-radiation threshold voltage are used to generate a two-point calibration curve that is stored, such as in the sensor-specific FRAM memory device. The two-point gamma-exposure calibration curve correlates the average, low-level pre-gamma threshold voltage of 4.25 V with a 0 kGy gamma-radiation level whereas the average, high-level threshold voltage of 4.75 V is correlated with a 35 kGy (+/−5%) gamma-radiation level if the certified gamma-radiation was carried at 35 kGy. If the gamma-radiation level is certified at some other level, then the certified level is correlated with the corresponding post-gamma average threshold voltage.

As an example, a FRAM chip can have a factory-specified supply voltage requirement of 5.00 Volts. FIG. 15 (y-axis) shows a number of supply voltage thresholds in excess of 5.00 Volts in the 35 kGy and 45 kGy exposure levels. The affected FRAMs would not be functional at a specified 5.00 Volt supply voltage. However, as has been determined in this disclosure, a supply voltage greater than the highest indicated threshold voltage will restore FRAM functionality. Thus a supply voltage between 5.250 and 5.500 Volts would safely ensure FRAM functionality at all indicated gamma-exposure levels. This is the basis for an electronically verifiable gamma-exposure meter as outlined herein. When a sensor is connected to a monitor, the gamma-exposure level stored in the sensor-specific memory device is displayed by the monitor indicating either a zero kGy gamma exposure level for a non-gamma-irradiated sensor or a positive kGy number that substantially coincides with the actual gamma exposure level for that sensor.

In addition, it is possible to conduct a pre-gamma memory check using a selected pattern (e.g., unique number sequence) written by the monitor into the FRAM device and stored in a reserved memory location. The monitor then issues a "Read" command and displays the stored memory content thereby confirming the accuracy of the Read/Write sequence. The pre-gamma memory check is carried out at a memory supply voltage (Vcc) of 5.25 and 5.50V.

The minimum memory threshold voltage (Vcc) is either known (e.g. 4.25 average, see FIG. 15) or is experimentally determined by stepping the Vcc from 4.00V to 5.25V and checking for the stored memory pattern after each voltage step increase. The lowest applied Vcc voltage that provides memory access and correctly displays the stored memory pattern is the pre-gamma irradiation Vcc of the tested memory device. The pre-gamma irradiation value of the minimum threshold voltage is stored in the on-sensor, gamma-stable memory.

The post-gamma memory check occurs after installation of the gamma-irradiated sensor/manifold. After hook-up of the sensor to the monitor, the initial sensor start-up sequence includes a re-testing of the Vcc by stepping the Vcc incrementally from 4.00V to 5.25V as outlined above. The lowest applied Vcc voltage that provides memory access and correctly displays the stored memory pattern is the post-gamma Vcc of the tested memory device. The post-gamma value of the Vcc is stored in a separate sensor memory location.

The sensor-specific, post-gamma irradiation threshold voltage is expected to exceed the pre-gamma irradiation threshold voltage by 0.25 to 0.75 volts at a 35 kGy gamma-irradiation level, see FIG. 15. The stored pre-gamma irradiation threshold voltage is associated with gamma-irradiation level of 0 kGy whereas the post-gamma irradiation threshold voltage represents the 35 kGy irradiation level. The gamma-irradiation level can be specified and applied within +/−5% of the specified exposure level. Thus, for a specified 35 kGy gamma-irradiation level, the actual exposure could range from 33.25 kGy to 36.75.

The aforementioned embodiments include a selection of novel sensor materials, innovative circuit designs which separate the analog and digital circuits, labeling to preserve sensor-specific information, and a user interface that includes supporting software and procedures to accommodate, retrieve, interpret and calculate sensor-specific information. These materials, circuits, and labeling, are designed to withstand the conditions of the sterilization methods used by the bio-pharmaceutical industry.

It will be understood that the embodiments of the present invention which have been described are illustrative of some of the applications of the principles of the present invention. Numerous modifications may be made by those skilled in the art without departing from the true spirit and scope of the invention.

The invention claimed is:

1. A single-use bio-solution processing sensor, comprising:
    a fluid conduit through which a biopharmaceutical solution flows during use of the sensor;
    an on-sensor memory device;
    a usage counter associated with the sensor;
    said usage counter includes a motion detector, the motion detector detects vibration corresponding to solution flow through the fluid conduit, and the memory device analyzes the vibration and designates the vibration as a counted sensor use event, whereupon the counted sensor use event is stored on the memory device and accumulates with prior or subsequent use events until a maximum use total stored on the memory device is attained; and
    the motion detector is an accelerometer that operates as a flow meter, whereby when a relatively non-compressible fluid flows through the fluid conduit a first accelerometer output is generated, and when a compressible fluid flows through the fluid conduit a second accelerometer output is generated, resulting in a differential between the first and second accelerometer outputs, thereby indicating an end to a cycle of a manifold within which the sensor is included.

2. The sensor according to claim 1, wherein said vibration is recognized as a counted sensor use only after having been maintained for a pre-selected time interval.

3. The sensor according to claim 1, wherein said memory device has sensor-specific serialization and traceability data retrievable from the memory device.

4. The sensor according to claim 1, further including a first input provision to disable the sensor once the maximum use total is attained and a second input provision to allow continued sensor use even after the maximum use total is attained.

5. The sensor according to claim 1, wherein said memory device analyzes the length of time that the detector detects vibration and stores the length of time as an amount of use time between said use threshold event and said end point of usage is stored in the memory device as a use amount that accumulates until the maximum use time total is attained.

6. The sensor according to claim 1, wherein the sensor includes an electrode at least partially positioned in said fluid conduit, and said electrode collects parameter data of the biopharmaceutical solution within the fluid conduit, the parameter data being used to calculate a solution property selected from the group consisting of electrical conductivity, pressure, temperature, pH, dissolved oxygen, turbidity, and combinations thereof.

7. The sensor according to claim 1, wherein said on-sensor memory device has a time event feature, said time event feature is initialized by achievement of a threshold event and is recognized as a counted sensor use after having been maintained for a pre-selected time interval, whereupon the counted sensor use is stored on the memory device and accumulates with prior or subsequent uses until a maximum use total is attained; and said time event feature and usage counter utilizing motion detection electronically interact to confirm total usage.

8. The sensor according to claim 1, further including a first input provision to disable the sensor once the maximum use total is attained.

9. The sensor according to claim 1, further including a second input provision to allow continued sensor use even after the maximum use total is attained.

10. The system according to claim 1, wherein said motion detector is an accelerometer on the base of the multiple-use interface.

11. The sensor according to claim 1, further including
    an on-sensor thermal fuse that is readable for transmission of information to the sensor for storage on the memory device, the thermal fuse being set with a threshold autoclave temperature at which the fuse trips, and the thermal fuse is electronically interrogatable for fuse tripping prior to its use in solution processing, thereby indicating successful autoclaving.

12. The sensor according to claim 11, wherein the thermal fuse has a closed circuit status, as set, at which the fuse is closed prior to having been subjected to the threshold autoclave temperature and an open circuit status at which the fuse is open upon being subjected to the threshold autoclave temperature.

13. The sensor according to claim 1, wherein the on-sensor memory device has an as-manufactured stored pre-gamma radiation threshold voltage and an as-manufactured stored post-gamma radiation threshold voltage greater in magnitude than a pre-gamma threshold radiation voltage, further including
    an on-sensor gamma-responsive component that informs the on-sensor memory device of voltage due to gamma radiation exposure, and exposure of the gamma sensor to gamma radiation shifts the voltage in a repeatable manner to indicate the sensor has been sterilized with gamma radiation.

14. The sensor in accordance with claim 13, wherein the on-sensor gamma-responsive component is a bipolar transistor.

15. The sensor in accordance with claim 13, wherein the on-sensor gamma-responsive component is a gamma-exposure meter associated with a FRAM chip having a factory-specified supply voltage requirement at which the FRAM chip functionality is restored with gamma radiation.

16. The sensor according to claim 15, wherein the pre-gamma radiation threshold voltage correlates to a zero kGy gamma radiation level, and the post-gamma irradiation threshold voltage correlates to a positive kGy gamma radiation level substantially corresponding to a gamma radiation exposure level for said sensor.

17. The sensor according to claim 16, wherein the average pre-gamma irradiation threshold voltage is 4.25+/−0.05 volts, and the average post-gamma irradiation threshold voltage is 4.75+/−0.05 volts, and wherein 4.25 volts correlates with zero kGy and 4.75 volts correlates with 35+/−5% kGy.

18. A dockable sensor system comprising a combination of a multiple-use user interface, a single-use bio-solution processing sensor module and a motion detector:
    the multiple-use interface having an electronic reception and transmission function and comprising a base having a docking location;
    the single-use sensor module comprising:
    a fluid conduit through which a biopharmaceutical solution flows during use of the sensor;

an on-sensor memory device;

a usage counter associated with the sensor;

said usage counter includes a motion detector, the motion detector detects vibration corresponding to changes in solution flow through the fluid conduit, and the memory device analyzes the vibration and designates the vibration as a counted sensor use event, whereupon the counted sensor use event is stored on the memory device and accumulates with prior or subsequent use events until a maximum use total stored on the memory device is attained; and the motion detector is an accelerometer that operates as a flow meter, whereby when a relatively non-compressible fluid flows through the fluid conduit a first accelerometer output is generated, and when a compressible fluid flows through the fluid conduit a second accelerometer output is generated, resulting in a differential between the first and second accelerometer outputs, thereby indicating an end to a cycle of a manifold within which the sensor is included.

19. The system according to claim 18, wherein said motion detector is an accelerometer on the base of the multiple-use interface.

20. The system according to claim 18, wherein said vibration is recognized as a counted sensor use event after having been maintained for a preselected time interval.

21. The system according to claim 18, wherein said usage counter utilizes a self-heating thermistor in operative communication with the fluid conduit and the memory device, and a counted sensor event occurs when the thermistor detects a change in temperature reading when compared with its temperature reading for air.

22. The sensor according to claim 18, wherein said on-sensor memory device has a time event feature, said time event feature is initialized by achievement of a threshold event and is recognized as a counted sensor use after having been maintained for a pre-selected time interval, whereupon the counted sensor use is stored on the memory device and accumulates with prior or subsequent uses until a maximum use total is attained; and said time event feature and usage counter utilizing motion detection electronically interact to confirm total usage.

23. The sensor according to claim 18, further including a first input provision to disable the sensor once the maximum use total is attained.

24. The sensor according to claim 18, further including a second input provision to allow continued sensor use even after the maximum use total is attained.

* * * * *